US010769467B2

(12) United States Patent
Hirai et al.

(10) Patent No.: US 10,769,467 B2
(45) Date of Patent: Sep. 8, 2020

(54) INFORMATION PROCESSING APPARATUS, INFORMATION PROCESSING SYSTEM, AND COMPUTER PROGRAM PRODUCT

(71) Applicant: KABUSHIKI KAISHA TOSHIBA, Tokyo (JP)

(72) Inventors: Ryusuke Hirai, Tokyo (JP); Yasunori Taguchi, Kanagawa (JP); Wataru Watanabe, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 0 days.

(21) Appl. No.: 15/894,271

(22) Filed: Feb. 12, 2018

(65) Prior Publication Data

US 2019/0026584 A1    Jan. 24, 2019

(30) Foreign Application Priority Data

Jul. 20, 2017  (JP) ................................. 2017-141230

(51) Int. Cl.
| G06K 9/00 | (2006.01) |
| G06K 9/20 | (2006.01) |
| G06K 9/62 | (2006.01) |
| A61N 5/10 | (2006.01) |
| G06F 3/0482 | (2013.01) |

(Continued)

(52) U.S. Cl.
CPC .......... G06K 9/2081 (2013.01); A61N 5/1049 (2013.01); A61N 5/1067 (2013.01); G06K 9/00208 (2013.01); G06K 9/6202 (2013.01); G06K 9/6215 (2013.01); A61N 2005/1061 (2013.01); A61N 2005/1074 (2013.01); G06F 3/0482 (2013.01); G06F 3/0488 (2013.01);

(Continued)

(58) Field of Classification Search
CPC .... A61N 2005/1061; A61N 2005/1074; A61N 5/1049; A61N 5/1067; G06F 3/0482; G06F 3/04845; G06F 3/0488; G06K 9/00208; G06K 9/2081; G06K 9/6202; G06K 9/6215
See application file for complete search history.

(56) References Cited

U.S. PATENT DOCUMENTS

2005/0053196 A1*  3/2005  Mostafavi ............ A61B 6/4441
                                                           378/98.12
2013/0121551 A1*  5/2013  Poulsen ............... A61N 5/1049
                                                              382/131

(Continued)

FOREIGN PATENT DOCUMENTS

| CN | 101639858 | 2/2010 |
| CN | 105989092 | 10/2016 |
| JP | 2016-131737 | 7/2016 |

OTHER PUBLICATIONS

English-language machine translation of CN101639858.

*Primary Examiner* — Xin Jia
(74) *Attorney, Agent, or Firm* — Nixon & Vanderhye, P.C.

(57) ABSTRACT

According to one embodiment, an information processing apparatus includes an input receiver, a template selector, and a tracker. The input receiver receives an input operation of a user. The template selector specifies at least one template out of a plurality of templates that are related to a shape of an object based on the input operation received by the input receiver. The tracker tracks the object in an image including the object by using the at least one template specified by the template selector.

19 Claims, 15 Drawing Sheets

(51) Int. Cl.
    *G06F 3/0488* (2013.01)
    *G06K 9/32* (2006.01)
    *G06F 3/0484* (2013.01)

(52) U.S. Cl.
    CPC .. *G06F 3/04845* (2013.01); *G06K 2009/3291* (2013.01)

(56) References Cited

U.S. PATENT DOCUMENTS

2016/0239972 A1   8/2016  Zhu et al.
2016/0364122 A1* 12/2016  Shimomura .......... G06F 17/248
2016/0364878 A1* 12/2016  Guo .................... G06K 9/6202
2019/0143146 A1*  5/2019  Fujii ....................... A61N 5/10

\* cited by examiner

FIG. 9

| TEMPLATE IDENTIFICATION INFORMATION | TEMPLATE IMAGE INFORMATION | CHARACTERISTIC AMOUNT ||||||| DEGREE OF SIMILARITY | SELECTION STATE |
|---|---|---|---|---|---|---|---|---|---|
| | | THICKNESS T | LENGTH L | ANGLE θ | ANGLE φ | ANGLE η | SIZE M | | |
| ... | ... | ... | ... | ... | ... | ... | ... | ... | ... |
| ID_(i-1) | ... | ... | ... | 90+α1 | ... | ... | ... | ... | ... |
| ID_i | ... | ... | ... | 90 | ... | ... | ... | ... | ... |
| ID_(i+1) | ... | ... | ... | 90-α2 | ... | ... | ... | ... | ... |
| ... | ... | ... | ... | ... | ... | ... | ... | ... | ... |
| ID_k | ... | ... | ... | +45 | ... | ... | ... | ... | ... |
| ... | ... | ... | ... | ... | ... | ... | ... | ... | ... |
| ID_(j-1) | ... | ... | ... | +α3 | ... | ... | ... | ... | ... |
| ID_j | ... | ... | ... | 0 | ... | ... | ... | ... | ... |
| ID_(j-1) | ... | ... | ... | -α4 | ... | ... | ... | ... | ... |
| ID_l | ... | ... | ... | -45 | ... | ... | ... | ... | ... |
| ... | ... | ... | ... | ... | ... | ... | ... | ... | ... |

| TEMPLATE SET IDENTIFICATION INFORMATION | TEMPLATE IDENTIFICATION INFORMATION | TEMPLATE IMAGE INFORMATION | CHARACTERISTIC AMOUNT | | | | | | DEGREE OF SIMILARITY | SELECTION STATE |
|---|---|---|---|---|---|---|---|---|---|---|
| | | | THICKNESS T | LENGTH L | ANGLE $\theta$ | ANGLE $\phi$ | ANGLE $\eta$ | SIZE M | | |
| ... | ... | ... | ... | ... | ... | ... | ... | ... | ... | ... |
| ID_Gi | ID_i-1 | ... | ... | ... | 90 | ... | ... | ... | ... | ... |
| | ID_i-2 | ... | ... | ... | ... | 90 | ... | ... | ... | ... |
| ... | ... | ... | ... | ... | ... | ... | ... | ... | ... | ... |
| ID_Gj | ID_j-1 | ... | ... | ... | 0 | ... | ... | ... | ... | ... |
| | ID_j-2 | ... | ... | ... | ... | 0 | ... | ... | ... | ... |
| ID_Gj* | ID_j-1 | ... | ... | ... | α5 | ... | ... | ... | ... | ... |
| | ID_j-2 | ... | ... | ... | ... | β1 | ... | ... | ... | ... |
| ... | ... | ... | ... | ... | ... | ... | ... | ... | ... | ... |
| ID_Gk | ID_j-1 | ... | ... | ... | +45 | ... | ... | ... | ... | ... |
| | ID_j-2 | ... | ... | ... | ... | −45 | ... | ... | ... | ... |
| ID_Gk* | ID_j-1 | ... | ... | ... | +45 | ... | ... | ... | ... | ... |
| | ID_j-2 | ... | ... | ... | ... | −45 | ... | ... | ... | ... |
| ... | ... | ... | ... | ... | ... | ... | ... | ... | ... | ... |

107a

INFORMATION PROCESSING APPARATUS, INFORMATION PROCESSING SYSTEM, AND COMPUTER PROGRAM PRODUCT

CROSS-REFERENCE TO RELATED APPLICATION

This application is based upon and claims the benefit of priority from Japanese Patent Application No. 2017-141230, filed Jul. 20, 2017; the entire contents of which are incorporated herein by reference.

FIELD

Embodiments described herein relate generally to an information processing apparatus, an information processing system, and a computer program product.

BACKGROUND

Information processing apparatuses detecting the position of an object using a technique of template matching by using an image acquired by imaging the object inside a subject is known. In the case of such a technique, when the number of templates is increased, the calculation load is increased, and there are cases in which it is difficult to achieve further improvement of tracking accuracy of the object.

BRIEF DESCRIPTION OF THE DRAWINGS

FIG. 9 is a diagram showing one example of content of a template information DB 107a according to the first embodiment;

FIG. 16 is a diagram showing one example of a content of a template information DB 107a according to the third modified example of the first embodiment;

DETAILED DESCRIPTION

Figure 1:
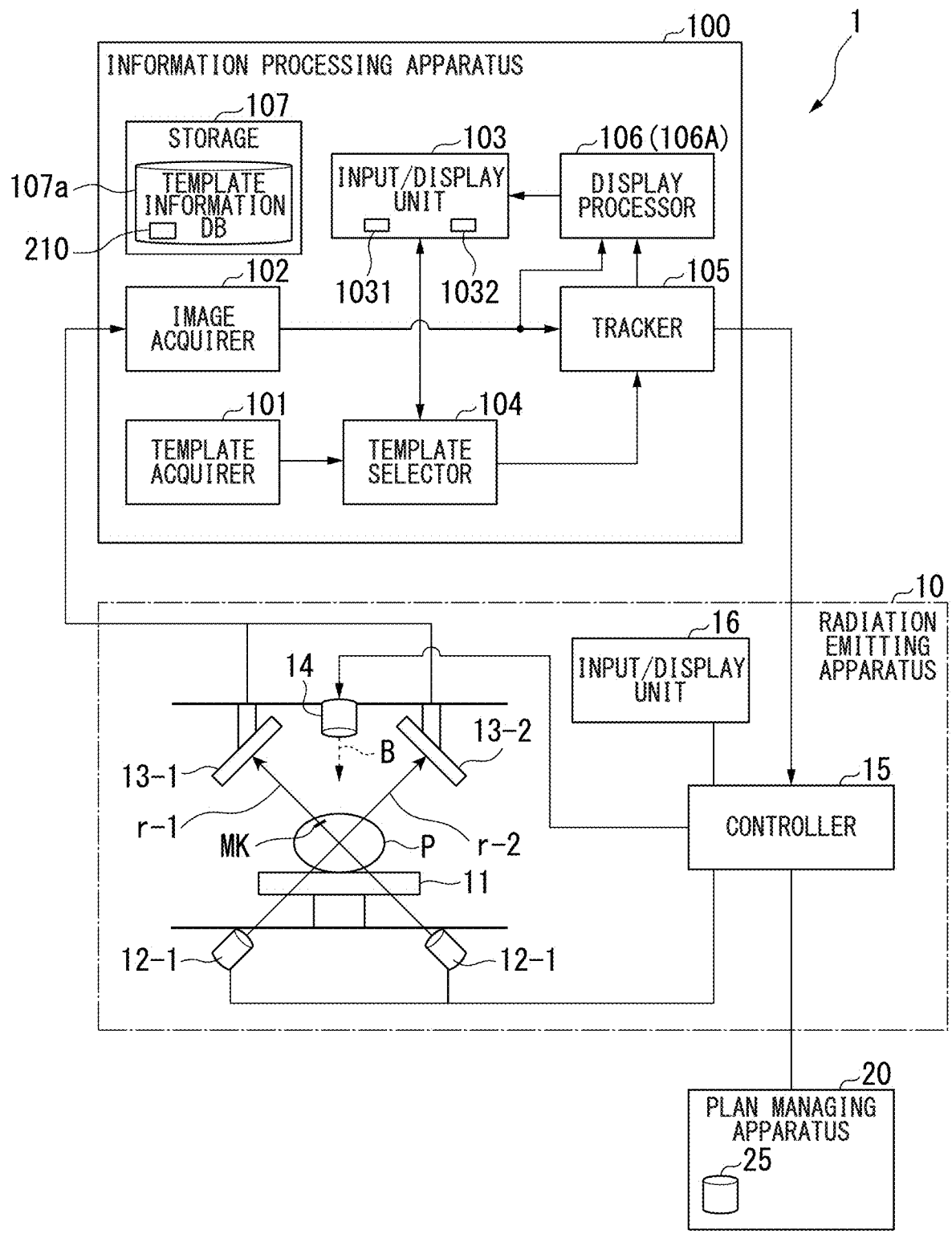
FIG. 1 is a diagram showing an example of the configuration of a medical treatment system 1 according to a first embodiment.

According to one embodiment, an information processing apparatus includes an input receiver, a template selector, and a tracker. The input receiver receives an input operation of a user. The template selector specifies at least one template out of a plurality of templates that are related to a shape of an object based on the input operation received by the input receiver. The tracker tracks the object in an image including the object by using the at least one template specified by the template selector.

Hereinafter, an information processing apparatus, an information processing system, and a computer program product according to embodiments will be described with reference to the drawings. In the following embodiments, an example in which an information processing apparatus, an information processing system, and a computer program product are applied to an apparatus and a system relating to a radiation treatment will be described. However, the information processing apparatus, the information processing system, and the computer program product are not limited to the examples described above and may be an information processing apparatus, an information processing system, and a computer program product applied to a different use other than medical treatments. In description presented below, same reference numerals will be attached to configurations having the same or similar functions. A duplicate description of the configurations may be omitted.

In the specification, the term "based on XX" represents "based at least on XX" and includes the case of being based on any other element in addition to XX. In addition, the term "based on XX" is not limited to "based directly on XX", but also represents "based on something that is acquired by an arithmetic operation or other process being performed on XX". Here, "XX" is an arbitrary element (for example, arbitrary information).

First Embodiment

FIG. 1 is a diagram showing an example of the configuration of a medical treatment system 1 including an information processing apparatus 100 according to a first embodiment. The medical treatment system 1, for example, is a treatment system used for a treatment of a radiation emission type. "Radiation rays" described here includes at least one of electromagnetic waves such as X rays and θ rays and particle beams such as a proton beam and a heavy particle beam. The medical treatment system 1 is one example of an "information processing system."

As shown in FIG. 1, the medical treatment system 1, for example, includes a radiation emitting apparatus 10 and an information processing apparatus 100. Although the radiation emitting apparatus 10 and the information processing apparatus 100 will be separately described here for convenience of description, the information processing apparatus 100 may be provided as a part of the radiation emitting apparatus 10. The medical treatment system 1, in relation with the radiation emitting apparatus 10 and the information processing apparatus 100, may further include a plan managing apparatus 20 that manages a treatment plan. Here, first, the radiation emitting apparatus 10 and the plan managing apparatus 20 will be described, and then the information processing apparatus 100 will be described.

Here, "subject" and "object" will be defined. The term "subject" broadly means a target body for information processing performed by the information processing apparatus 100. For example, "subject" means a target for which an object detecting process is performed by the information processing apparatus 100. In a case in which the information processing apparatus 100 is used in the medical treatment system 1, the "subject," for example, is a patient. The term "object" may be a tumor (lesion) or the like in a tissue of a subject or a marker or the like placed inside a subject by a percutaneous treatment. In this embodiment, the marker is a metal marker. The marker, for example, has a non-spherical shape such as a bar shape or a wedge shape and may have any other shape. Hereinafter, an example in which a metal marker inside a subject corresponds to an object is shown. In other words, in description presented below, each instance of "marker" may be replaced with "object."

[Radiation Emitting Apparatus]

The radiation emitting apparatus 10 is an apparatus that emits radiation toward a subject P. The radiation emitting apparatus 10, for example, includes a bed 11, radiation sources (fluoroscopic radiation emitters) 12-1 and 12-2, radiation detectors 13-1 and 13-2, an emission gate 14 (treatment beam emitter), a controller 15, and an input/display unit 16.

A subject P is fixed to the bed 11 using a fixing tool not shown in the drawing. The subject P is supported by the fixing tool such that the body posture of the subject P does not change.

The radiation source 12-1 emits a fluoroscopic radioactive ray r-1 to the subject P. The radiation source 12-2 emits a fluoroscopic radioactive ray r-2 to the subject P from a position different from that of the radiation source 12-1 (i.e., different angle from that of the radiation source 12-1). The fluoroscopic radiation rays r-1 and r-2, for example, are X rays.

The radiation detector 13-1 is directed toward the radiation source 12-1 with the subject P interposed therebetween. The radiation detector 13-1 includes detection elements arranged in an array pattern and detects the fluoroscopic radioactive ray r-1 emitted from the radiation source 12-1. The radiation detector 13-1 detects the energy of the radioactive ray r-1 and digitizes the energy to generate a first image (i.e., first fluoroscopic image). The radiation detector 13-1 outputs the generated first image to an image acquirer 102 of the information processing apparatus 100. Here, the generation of the first image may be performed by the image acquirer 102 receiving a detection result acquired by the radiation detector 13-1.

The radiation detector 13-2 is directed toward the radiation source 12-2 with the subject P interposed therebetween. The radiation detector 13-2 includes detection elements arranged in an array pattern and detects the fluoroscopic radioactive ray r-2 emitted from the radiation source 12-2. The radiation detector 13-2 detects the energy of the radioactive ray r-2 and digitizes the energy to generate a second image (i.e., second fluoroscopic image). The radiation detector 13-2 outputs the generated second image to the image acquirer 102 of the information processing apparatus 100. Here, the generation of the second image may be performed by the image acquirer 102 receiving a detection result acquired by the radiation detector 13-2.

Each of the radiation detectors 13-1 and 13-2 is a flat panel detector (FPD), an image intensifier, a color image intensifier, or the like. Although two sets of radiation sources and radiation detectors are shown in FIG. 1, the number of sets is not limited thereto. Thus, the radiation emitting apparatus 10 may include three or more sets of radiation sources and radiation detectors. Hereinafter, for the convenience of description, each of the first image and the second image will be described as an image IM except for a case in which the first image and the second image are distinguished.

The emission gate 14 emits a treatment beam B toward the subject P in a treatment stage. The treatment beam B, for example, includes at least one of X rays, γ rays, an electron beam, a proton beam, a neutron beam, a heavy particle beam, and the like. The treatment beam B is an example of "energy." The emission gate 14 is one example of an "emitter." Only one emission gate 14 is shown in FIG. 1. However, the radiation emitting apparatus 10 may include a plurality of emission gates 14. In addition, the position of the emission gate 14 is not limited to the position shown in FIG. 1 but may be a position that is substantially in parallel with the subject P in an substantially horizontal direction.

The controller 15, for example, is realized by a hardware processor such as a central processing unit (CPU) executing a computer program (i.e., software program). The computer program may be embodied on a non-transitory computer-readable storage medium. In addition, the controller 15 may be realized by hardware (i.e., circuitry) such as a large scale integration (LSI), an application specific integrated circuit (ASIC), a field-programmable gate array (FPGA), or a graphics processing unit (GPU) and may be realized by software program and hardware in cooperation. The controller 15, for example, may have a configuration that is substantially the same as the hardware configuration of the information processing apparatus 100 to be described later with reference to FIG. 2.

The controller 15 executes control of the radiation sources 12-1 and 12-2 to emit the fluoroscopic radioactive rays r-1 and r-2 at a predetermined interval (i.e., at a predetermined period) on the basis of a treatment plan to be described later. In addition, the controller 15 executes control of the emission gate 14 to emit the treatment beam B on the basis of the treatment plan. For example, the controller 15 executes control of the emission gate 14 on the basis of the position of a marker MK tracked by a tracker 105 of the information processing apparatus 100 to be described later.

The input/display unit 16, for example, includes an input device such as a touch panel, a general-purpose keyboard, a mouse, dedicated keys, a dial, or a microphone and a display device such as a liquid crystal display or an organic electroluminescence (organic EL) display. The input/display unit 16 displays an image or the like output from the information processing apparatus 100. In addition, the input/display unit 16 may be integrated with an input/display unit 103 of the information processing apparatus 100 to be described later.

[Plan Managing Apparatus]

The plan managing apparatus 20 includes a plan data storage 25 that stores a treatment plan in a radiation treatment. The plan data storage 25 is, for example, a hard disk drive (HDD), a flash memory, a read only memory (ROM), or the like. Here, the "treatment plan" will be described. The treatment plan includes energy, an emission direction, the shape of an emission range, distribution of doses, in which radiation is emitted a plurality of times, and the like of a radiation ray (for example, the treatment beam B) emitted to the subject P. In generation of a treatment plan, for a computer tomography (CT) image captured at the time of generating the treatment plan, a boundary between a tumor and a normal area and boundaries with significant organs disposed in the periphery of the tumor are designated, and the direction and the intensity of the treatment beam B to be emitted are determined on the basis of a depth of the position of the tumor from the body surface and the size of the tumor. At this time, the position of a marker MK placed inside the subject P is also registered in the treatment plan.

By designating the boundary between the tumor and the normal area, the position and the volume of the tumor are designated. This volume is called a gross target volume (GTV), a clinical target volume (CTV), an internal target volume (ITV), a planning target volume (PTV), or the like. The GTV is the volume of a tumor that can be checked from an image with the naked eyes and represents a portion needed to be irradiated with a sufficient dose in a curative treatment. The CTV is a volume including a GTV and a latent tumor to be treated. The ITV is a volume acquired by adding a margin to the CTV in consideration of movement of the CTV according to a predicted biological motion or the like. The PTV is a volume acquired by adding a margin to the ITV in consideration of an error in the positioning at the time of the treatment. Accordingly, among these volumes, there is a relation of GTV⊆CTV⊆ITV⊆PTV. In this way, a margin in consideration of an error having a possibility of occurring when an actual treatment that is set in a treatment plan is performed is added, whereby an emission field of the treatment beam B is determined. As such an error, for example, there is a deviation in the position of the subject P in the positioning of the subject P.

[Information Processing Apparatus]

In a case in which a tumor and a marker MK of the subject P move in accordance with the respiration of the lungs or liver or the motion of a heartbeat, even when the position of the bed 11 is adjusted, the position of a tumor that is an emission target is moved. In such a case, a method in which the treatment beam B is emitted by specifying the position of the tumor that is the emission target is used. As examples of such an emission method, there are tracking emission in which a tumor (or a marker MK) is tracked, and the treatment beam B is emitted to a moving tumor, ambush emission in which, when a tumor (or a marker MK) comes to a position set in the treatment plan, the treatment beam B is emitted, or the like. Such an emission method is called a respiration-synchronized emission method or the like.

The information processing apparatus 100 according to this embodiment is, for example, an apparatus used in the respiration-synchronized emission method as described above and is an apparatus that tracks a marker MK inside a subject P on the basis of an image IM acquired from the radiation emitting apparatus 10. The information processing apparatus 100, for example, includes a template acquirer 101, an image acquirer 102, an input/display unit 103, a template selector 104, a tracker 105, a display processor 106, and a storage 107.

Such constituent elements, for example, are realized by a hardware processor such as a CPU executing a computer program (i.e., software program). The computer program may be embodied on a non-transitory computer-readable storage medium. Some or all of such constituent elements may be realized by hardware (i.e., circuitry) such as an LSI, an ASIC, an FPGA, or a GPU or may be realized by software and hardware in cooperation. The storage 107, for example, is an HDD, a flash memory, a ROM, or the like.

Figure 2:
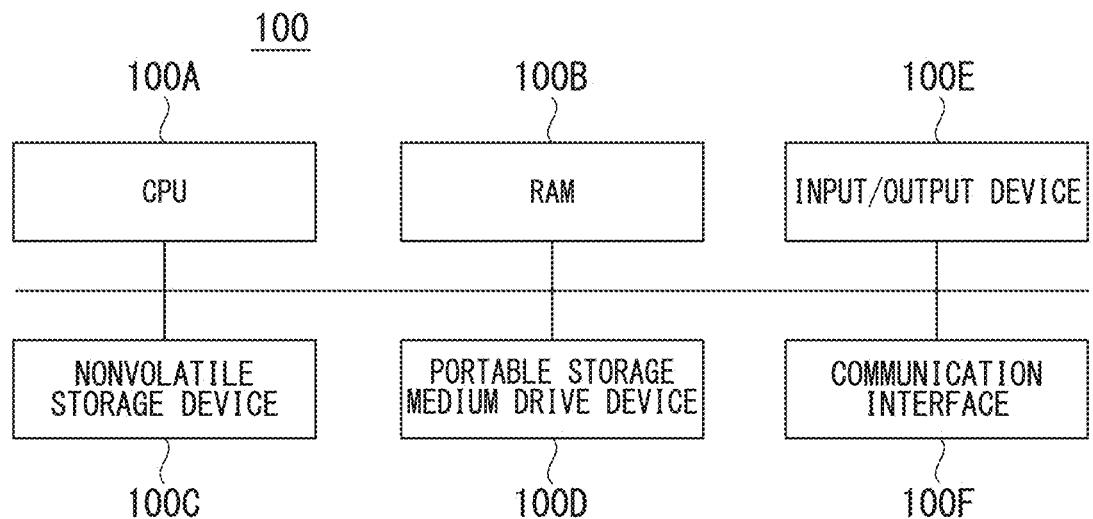
FIG. 2 is a diagram showing an example of the hardware configuration of an information processing apparatus 100 according to the first embodiment.

FIG. 2 is a diagram showing an example of the hardware configuration of the information processing apparatus 100. The information processing apparatus 100, for example, includes a CPU 100A, a random access memory (RAM) 100B, a nonvolatile storage device 100C, a portable storage medium drive device 100D, an input/output device 100E, and a communication interface 100F. The information processing apparatus 100 may include an arbitrary processor such as a GPU instead of the CPU 100A. Some of the constituent elements shown in FIG. 2 may be omitted.

The CPU 100A expands a computer program stored in the nonvolatile storage device 100C or a computer program stored in a portable-type storage medium loaded in the portable storage medium drive device 100D into the RAM 100B and executes the computer program, thereby performing various processes to be described below. The RAM 100B is used as a working area by the CPU 100A. The nonvolatile storage device 100C, for example, is an HDD, a flash memory, a ROM, or the like. In the portable storage medium drive device 100D, a portable-type storage medium such as a DVD, a compact disc (CD), an SD (trademark) card, or the like is loaded. The input/output device 100E, for example, includes a keyboard, a mouse, a touch panel, a display device, and the like. The communication interface 100F functions as an interface when the information processing apparatus 100 communicates with another apparatus.

In FIG. 1, the template acquirer 101 acquires a plurality of templates 210 relating to a marker MK (i.e., object) disposed inside the subject P. Here, "template" means data representing a typical shape of a certain element (in this embodiment, the marker MK disposed inside the subject P). In this embodiment, "template" means data representing an outer shape of an image of the marker MK (hereinafter referred to as a "marker image MKI") appearing in an image IM acquired by the image acquirer 102. The "marker image MKI" is a projected image of the marker MK seen from a certain position (for example, the position of the radiation source 12-1 or 12-2). In addition, the term "acquisition of a template" includes any one of a case in which the template acquirer 101 generates a template 210 and a case in which a template 210 generated by another apparatus is acquired by being received by the template acquirer 101. The template acquirer 101 may directly output the plurality of templates 210 that have been acquired to the template selector 104, the tracker 105, and the display processor 106 or may store the templates in the template information DB 107a of the storage 107. The plurality of templates 210 stored in the template information DB 107a can be read by the template selector 104, the tracker 105, and the display processor 106. In addition, in description presented here, an operation of reading information stored once in the template information DB 107*a* from the template information DB 107*a* corresponds to "acquisition of a template" as well.

As types of the template 210 as described above, for example, there may be templates 210 in which the posture of the marker MK on a two-dimensional plane is considered and may be templates 210 in which the posture of the marker MK in a three-dimensional space is considered. In this embodiment, an example in which the marker MK is a bar-shaped marker will be employed for the description.

Figure 3:
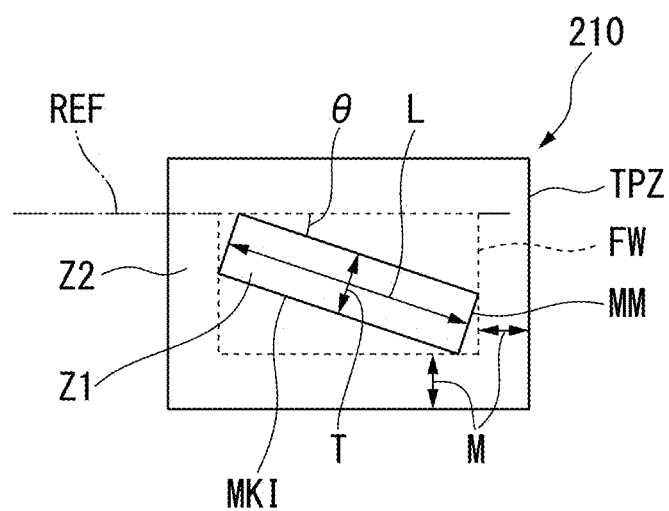
FIG. 3 is a diagram showing one example of a template 210 in which the posture of a marker MK in a two-dimensional plane is considered according to the first embodiment.

FIG. 3 is a diagram showing one example of the template 210 in which the posture of the marker MK in a two-dimensional plane is considered. The template 210 includes a rectangle MM corresponding to the outer shape (i.e., outer line) of the marker image MKI. In other words, the inner side of the rectangle MM is an area (a first area Z1; a marker correspondence area) of the template 210 which corresponds to the marker image MKI. On the other hand, the outer side of the rectangle area MM is an area (a second area Z2) of the template 210 which corresponds to a position deviating from the marker image MKI. In FIG. 3, "L" represents the length of the long side of the rectangle MM. "L" corresponds to the length of the marker image MKI in the longitudinal direction. In FIG. 3, T represents the length of the short side of the rectangle MM. T corresponds to the thickness of the marker image MKI. In FIG. 3, θ represents the inclination of the rectangle MM with respect to a reference line REF. The reference line REF is a segment extending in a specific direction set in advance with respect to the template 210. In other words, θ represents the direction of the marker MK on a two-dimensional plane. A rectangle FW is a rectangle that is parallel to the reference line REF and represents a rectangle that is circumscribed about the rectangle MM. In FIG. 3, M represents a margin of the rectangle FW. M is a quantity that sets the size of the template 210. In other words, a length acquired by adding 2M to the length of each side of the rectangle FW is the size of the template 210, and the outer shape TPZ of the template 210 is defined. The template acquirer 101, for example, generates a plurality of templates 210 by variously changing θ, thereby acquiring the plurality of templates 210 corresponding to various directions of the marker MK.

Figure 4:
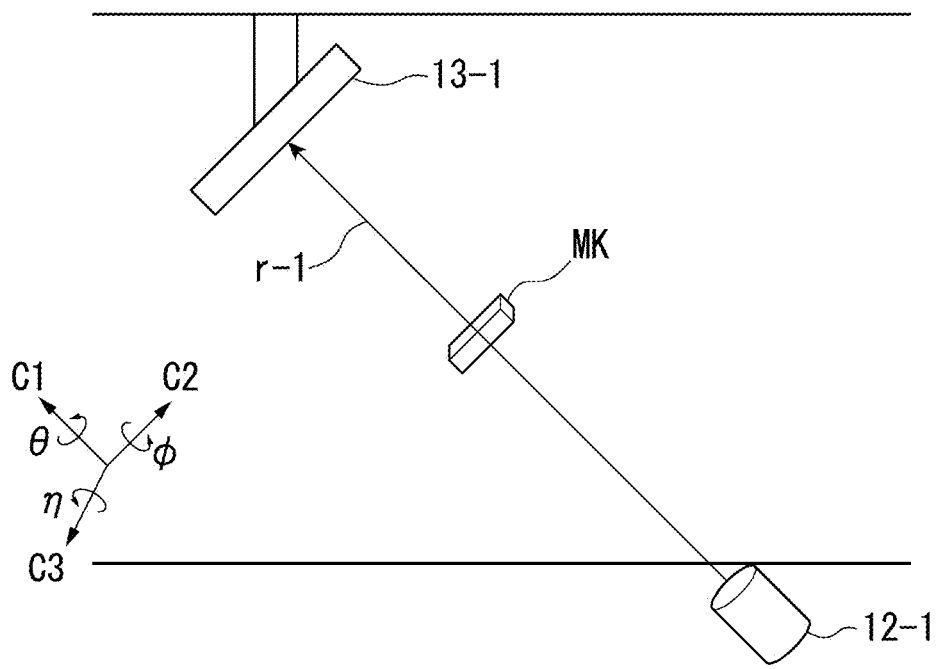
FIG. 4 is a diagram showing a template 210 in which the posture of a marker MK in a three dimensional space is considered according to the first embodiment.

FIG. 4 is a diagram showing the template 210 in which the posture of the marker MK in a three dimensional space is considered. FIG. 4 shows an appearance in which only the radiation source 12-1, the radiation detector 13-1, and the radioactive ray r-1 are extracted from the radiation emitting apparatus 10 shown in FIG. 1, and the marker MK having a bar shape is virtually arranged inside a three-dimensional space. As shown in FIG. 4, the template acquirer 101 acquires the plurality of templates 210 corresponding to various directions of the marker MK (i.e., various postures in the three-dimensional space) by generating the plurality of templates 210 acquired by variously changing θ, φ, and η that are the amounts of rotation around three axes C1, C2, and C3 that are orthogonal to each other. The axis C1 is, for example, an axis in the direction of the course of the radioactive ray r-1. The template acquirer 101 generates the plurality of templates 210 on the basis of a three-dimensional shape of the marker MK. In addition, for elements such as the rectangle MM, the first area Z1, the second area Z2, the length L, the width T, the size M, and the like described above, definitions that are similar to the definitions described above may be also used in the template 210 in which the posture in the three dimensional space is considered.

In addition, in any one case of the templates 210 in which the posture in the two-dimensional plane is considered and a case of the templates 210 in which the posture in the three-dimensional space is considered, if a plurality of radiation sources and a plurality of radiation detectors are present, a set of templates 210 corresponding to a set of marker images MKI detected by one set of radiation detectors configured by a plurality of radiation detectors may be prepared.

In addition, the template acquirer 101 acquires one or more similar templates 250 acquired by finely changing one or more parameters (for example, the posture parameters (θ, φ, and η)) defining the template 210 on the basis of the content of the template 210 selected or specified by the template selector 104. The template acquirer 101 outputs information representing one or more acquired similar templates 250 to the tracker 105. This content will be described later in detail.

In FIG. 1, the image acquirer 102 receives the images IM of the subject P from the radiation detectors 13-1 and 13-2, thereby acquiring the images IM of the subject P. The image IM of the subject P is an image that represents the inside of the body of the subject P and, for example, is a fluoroscopic image of the subject P. In the image IM of the subject P, the marker image MKI appears. Here, the marker MK is formed of metal. X rays used when the image IM is captured are easily absorbed by a metal. For this reason, in the image IM of the subject P, a portion corresponding to the marker image MKI is displayed darker than the periphery thereof. The image acquirer 102 outputs the acquired image IM of the subject P to the tracker 105 and the display processor 106.

The input/display unit 103, for example, includes an input receiver 1031 and a display 1032. The input receiver 1031, for example, is an input device such as a touch panel, a general-purpose keyboard, a mouse, dedicated keys, a dial, or a microphone. The input receiver 1031 receives a user's input operation. The "user's input operation" is not limited to an operation of operating a touch panel or a keyboard and may be an audio input to a microphone. In this embodiment, the input receiver 1031 receives a user's selection operation of selecting (i.e., designating) one or more templates 210 out of the plurality of templates 210. In this embodiment, the input receiver 1031 receives the user's selection operation of selecting one or more templates 210 out of two or more templates 210 that are displayed on the display 1032.

The display 1032 is a display device such as a liquid crystal display or an organic EL display. The display 1032 includes a display screen that can be viewed by a user during an input operation for the input receiver 1031. In addition, a user terminal device such as a notebook personal computer or a tablet terminal device may be communicably connected to the information processing apparatus 100 in a wired or wireless manner. In such a case, the input/display unit 103 may not include an input device and a display device. In such a case, the input receiver 1031 is a receiver that receives the user's input operation by receiving content of the user's input operation input to the user terminal device from the user terminal device.

The template selector 104 selects or specifies templates 210 corresponding to a number less than the number of a plurality of templates 210, that is, at least one template 210 (hereinafter referred to as a "selection template 230") out of the plurality of templates 210 acquired by the template acquirer 101. The selection template 230 is a template used for tracking the marker MK by the tracker 105. For example, the template selector 104 selects at least one selection template 230 on the basis of the image IM acquired by the image acquirer 102. An example in which the selection template 230 is selected on the basis of the image IM acquired by the image acquirer 102 will be described in detail with reference to a modified example of this embodiment. In this embodiment, the template selector 104 selects at least one selection template 230 on the basis of a user's input operation received by the input receiver 1031. For example, the template selector 104 specifies at least one selection template 230 on the basis of a user's selection operation of selecting one or more selection templates 230 that is received by the input receiver 1031. For example, the template selector 104 acquires identification information (for example, an identification ID registered in correspondence with each template 210) used for identifying one or more selection templates 230, which is received by the input receiver 1031, from the input receiver 1031 and collates templates 210 corresponding to the identification information among the plurality of templates 210, thereby specifying the selection templates 230 selected by the user.

Figure 5:
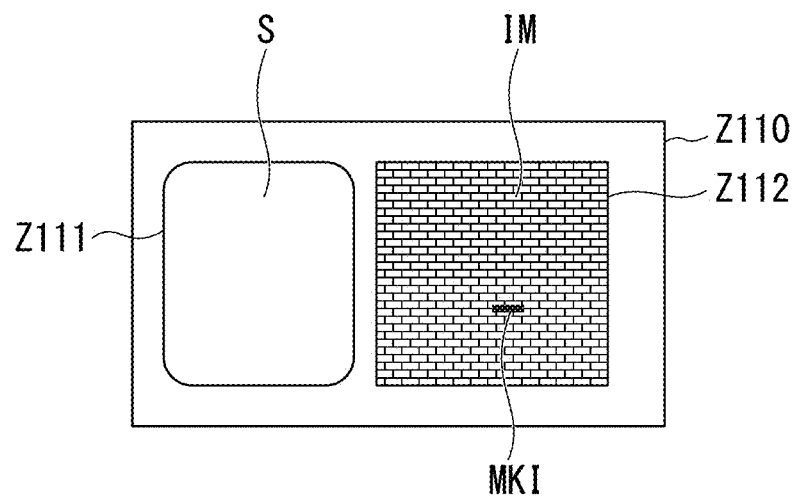
FIG. 5 is a diagram showing one example of an operation screen Z110 displayed on a display 1032 according to the first embodiment.

FIG. 5 is a diagram showing one example of an operation screen Z110 displayed on the display 1032. As shown in FIG. 5, the operation screen Z110 includes a template selection image display area Z111 and an image display area Z112. At least the template selection image display area Z111 and the image display area Z112 are arranged to be aligned on the operation screen Z110. In the template selection image display area Z111, a template selection screen S is displayed under the control of the display processor 106. On the template selection screen S, two or more candidate templates 220 included in the plurality of templates 210 (hereinafter referred to as "candidate templates 220") acquired by the template acquirer 101 are displayed. On the other hand, in the image display area Z112, the image IM acquired by the image acquirer 102 is displayed under the control of the display processor 106. The image IM acquired by the image acquirer 102 includes the marker image MKI of the inside of the subject P.

The layout of the operation screen Z110 is not limited to the example described above. For example, the arrangement positions of the template selection image display area Z111 and the image display area Z112 are not limited to the example described above. In addition, information other than the information described above may be displayed in the operation screen Z110. For example, a CT image, a DRR, information relating to the subject P, and the like may be displayed. The information processing apparatus 100 may display the template selection screen S and the image IM in different windows instead of displaying the template selection screen S and the image IM in the operation screen Z110 together. In addition, the display 1032 may separately include a first monitor displaying the template selection screen S and a second monitor displaying the image IM.

Figure 6:
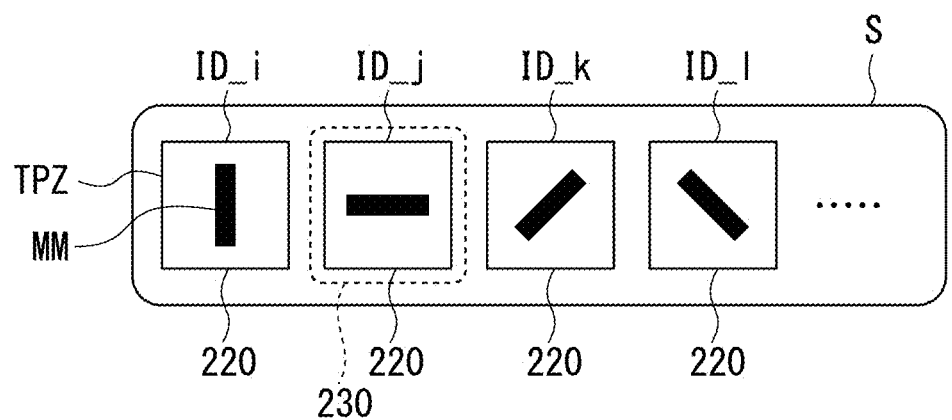
FIG. 6 is a diagram showing one example of content of a template selection screen S according to the first embodiment.

FIG. 6 is a diagram showing one example of the content of the template selection screen S. As shown in FIG. 6, a plurality of candidate templates 220 that are visually different from each other are displayed on the template selection screen S. For example, the plurality of candidate templates 220 have different directions of the rectangles MM representing a marker correspondence area in the longitudinal direction.

The plurality of candidate templates 220 shown in FIG. 6 are a plurality of templates acquired by sequentially changing the directions of the rectangles MM disposed inside outer shapes TPZ of the templates. For example, each candidate template 220 is a template generated by changing at least one of the parameters ($\theta$, $\varphi$, and $\eta$) representing the posture of the marker MK in accordance with a predetermined rule. Each of the parameters ($\theta$, $\varphi$, and $\eta$) is one example of the parameter defining the template 210. The display order of the candidate templates 220 may be arranged in a direction in which the parameters ($\theta$, $\varphi$, and $\eta$) are changed in accordance with the predetermined rule described above. Changes in the parameters ($\theta$, $\varphi$, and $\eta$) may be substantially continuous or at a predetermined interval such as an interval of 15 degrees.

In this embodiment, the display processor 106 further displays the image IM including the marker image MKI of the inside of the subject P acquired by the image acquirer 102 on the image display area Z112. Then, the input receiver 1031 receives a user's selection operation of selecting one or more selection templates 230 out of two or more candidate templates 220 displayed on the template selection screen S in the state in which the image IM including the marker image MKI of the inside of the subject P is displayed in the image display area Z112 by the display processor 106. In other words, a user selects a selection template 230 having a high degree of similarity for the marker image MKI out of the candidate templates 220 displayed in the template selection screen S while observing the marker image MKI disposed inside the image IM. As a method used in the selection operation, a user may press a button displayed on the operation screen Z110 to select a selection template 230 using a mouse or the like. Alternatively, as a method used in the selection operation, in a case in which a touch panel superimposed on the template selection screen S is provided, a selection template 230 may be selected by touching a specific portion of the template selection screen S in which the selection template 230 is displayed.

In this way, the template selector 104 specifies at least one selection template 230 on the basis of a user's selection operation. The template selector 104 outputs information representing the specified selection template 230 to the tracker 105. Here, the "information representing a template" may be image data of the template or identification information used for identifying the template.

The tracker 105 tracks the marker MK (for example, the position of the marker MK) by using the image IM acquired by the image acquirer 102 and at least one selection template 230 that is selected or specified by the template selector 104. In this embodiment, the tracker 105 tracks the position of the marker MK in the image IM using the selection template 230 by using a template matching technique.

Figure 7:
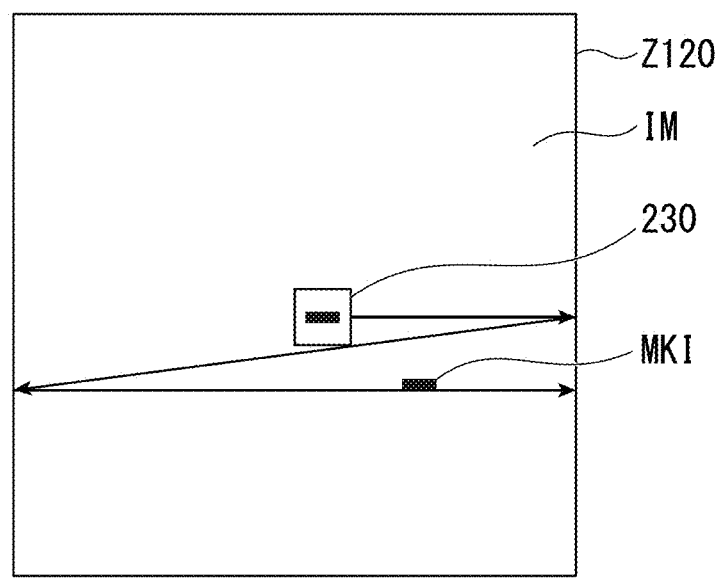
FIG. 7 is a diagram showing a tracking process of the position of a marker MK according to the first embodiment.

FIG. 7 is a diagram showing a tracking process of the position of the marker MK. The tracker 105 superimposes (i.e., composes) the selection template 230 onto the image IM acquired by the image acquirer 102 at a predetermined interval (i.e., predetermined period) and scans the selection template 230 at a predetermined range (i.e., calculation area). The predetermined range described above may be the whole area of the image IM or a partial area of the image IM. For example, the tracker 105 may limit the predetermined range described above to include the vicinity of the trajectory of the marker MK on the basis of the position of the marker MK acquired in a past treatment.

The calculation area described above represents a range for which the degree of similarity between an area of the image IM overlapping with the selection template 230 and the selection template 230 is calculated. For example, the tracker 105 calculates the degree of similarity between the image IM and the selection template 230 in the calculation area and specifies a position at which the degree of similarity is a threshold or more and the degree of similarity is a maximum as the position of the marker MK in the image IM. A method of calculating the degree of similarity performed by the tracker 105 may be on the basis of a normalized cross correlation, a mutual information amount or the like, in each of which a correlation between the image IM and the selection template 230 is acquired for each pixel. In this embodiment, the tracker 105 uses the degree of separation represented below as an index of the degree of similarity.

Figure 8:
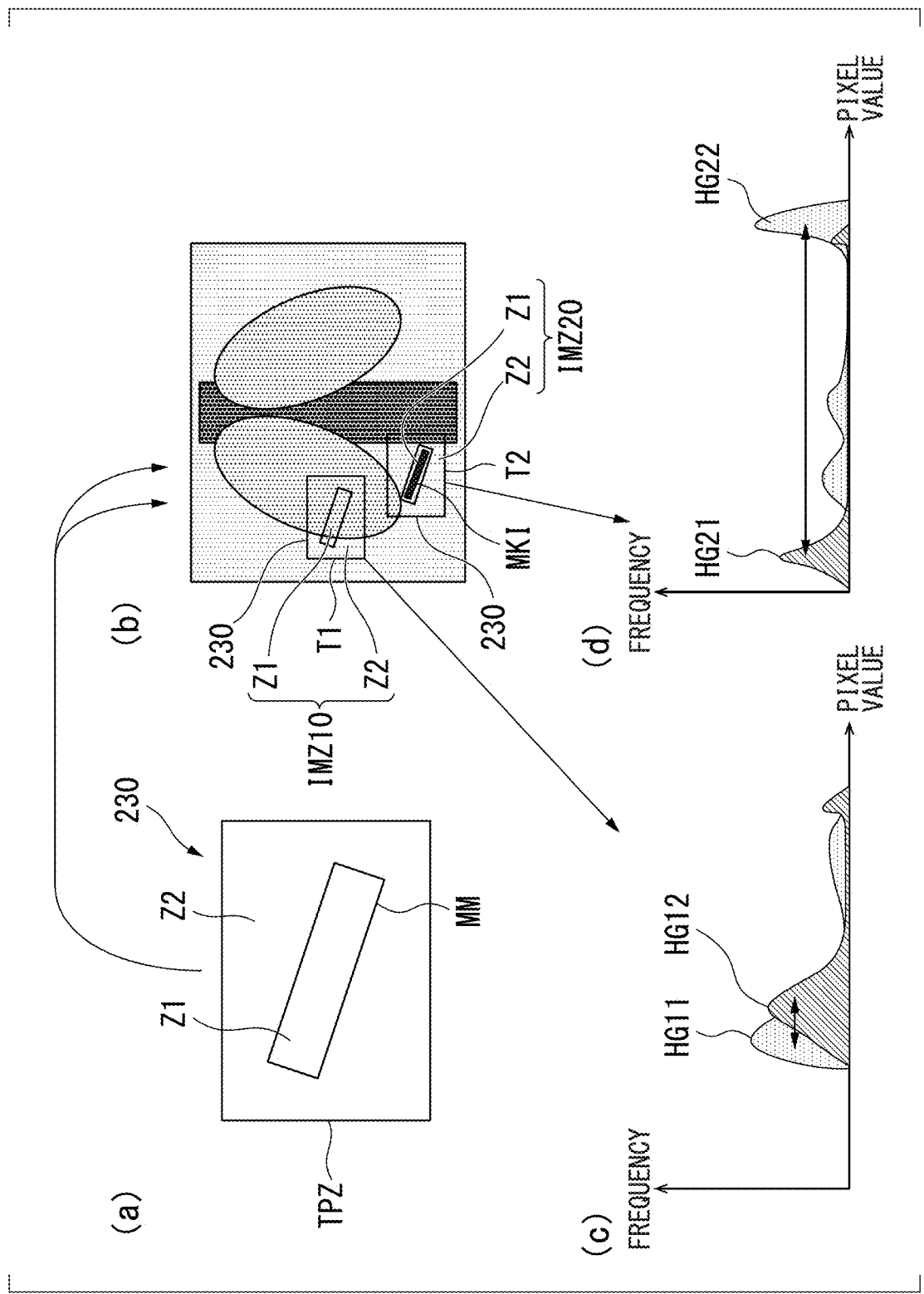
FIG. 8 is a diagram showing a process of calculating the degree of separation according to the first embodiment.

FIG. 8 is a diagram showing a process of calculating the degree of separation. (a) in FIG. 8 shows one example of the selection template 230. An inner area of the outer shape TPZ of the selection template 230 is divided into a first area Z1 surrounded by the rectangle MM and a second area Z2 other than the first area. The first area Z1 is an area corresponding to the marker image MKI. The second area Z2 is an area not corresponding to the marker image MKI.

(b) in FIG. 8 shows the selection template 230 arranged at a first position T1 and the selection template 230 arranged at a second position T2 for the image IM acquired by the image acquirer 102. The first position T1 is a position at which the selection template 230 and the marker image MKI do not overlap with each other. The second position T2 is a position at which the selection template 230 and the marker image MKI overlap with each other.

(c) in FIG. 8 shows a luminance distribution (i.e., pixel values) of a composed image IMZ10 acquired by composing the image IM and the selection template 230 in a case in which the selection template 230 is arranged at the first position T1. As shown in (c) in FIG. 8, in a case in which the selection template 230 is arranged at the first position T1, histograms of pixel values of the first area Z1 and the second area Z2 at the first position T1 represent the same tendency. In other words, differences between the histogram HG11 of the pixel values of the first area Z1 and the histogram HG12 of the pixel values of the second area 2 (for example, a difference between pixel values representing maximum values of the frequencies) are less than a predetermined threshold.

(d) in FIG. 8 shows a luminance distribution (i.e., pixel values) of a composed image IMZ20 acquired by composing the image IM and the selection template 230 in a case in which the selection template 230 is arranged at the second position T2. As shown in (d) in FIG. 8, in a case in which the selection template 230 is arranged at the second position T2, the histograms of pixel values of the first area Z1 and the second area Z2 at the second position T2 represent different tendencies. In other words, the two histograms are separated from each other. In other words, differences (for example, differences between pixel values representing maximum values of the frequency) between the histogram HG21 of the pixel values of the first area Z1 and the histogram HG22 of the pixel values of the second area Z2 are the threshold described above or more.

This is because, in the histogram HG21 of a case in which the first area Z1 and the marker image MKI overlap with each other, the frequency of a dark pixel is higher in the first area Z1 than in the second area Z2. On the other hand, in the second area Z2, the frequency of a bright pixel is relatively high, and the tendency of separation from the first area Z1 is outstanding. In contrast to this, in a histogram of a case in which the first area Z1 does not overlap with the marker image MKI, there is not a large difference between the tendencies of the distributions of frequencies of the first area Z1 and the second area Z2. In this way, by analyzing the distributions of brightness for each analysis unit (pixel) for the two areas Z1 and Z2 disposed inside the selection template 230, it can be determined whether or not the position of the selection template 230 is a position corresponding to the position of the marker MK.

For example, the tracker 105 expresses the degree of separation of the histogram in a numeral value by using a Fisher's discrimination criterion technique. In the process performed by the tracker 105, a ratio between an average of dispersion (i.e., intra-class dispersion) of pixel values (i.e., luminance levels) of the inside of each of the first area Z1 and the second area Z2 and dispersion (i.e., inter-class dispersion) of pixel values (i.e., luminance levels) between the first area Z1 and the second area Z2 is calculated. This ratio is used as the degree of separation.

According to the configuration described above, the tracker 105 detects the position of the marker MK by using the selection template 230, thereby tracking the position of the marker MK. The tracker 105 outputs information representing the position of the tracked marker MK to the display processor 106.

The display processor 106 is a controller controlling the display of the display 1032. The display processor 106 generates information representing a desired content to be displayed on the display 1032 and outputs the generated information to the display 1032, thereby displaying the desired content on the display 1032.

In a stage of selecting a template 210, the display processor 106 displays one or more candidate templates 220 included in a plurality of candidate templates 220 relating to the marker MK disposed inside the subject P on the display 1032. In addition, the display processor 106 displays the image IM acquired by the image acquirer 102 on the display 1032.

In a tracking stage of the marker MK using the tracker 105, the display processor 106 displays information representing the position of the marker MK that is tracked by the tracker 105 on the display 1032. For example, the display processor 106 displays the position of the marker MK that is tracked by the tracker 105 on the display 1032 in association with the image IM acquired by the image acquirer 102. Here, the term "associated display," for example, means that the display representing the position of the marker MK that is tracked by the tracker 105 is displayed to be superimposed on the image IM. The display processor 106 may display the template 210 used for tracking in the middle of the tracking of the marker MK using the tracker 105. In such a case, the position of the template 210 may be a position superimposed on the image IM or a position arranged to be aligned with the image IM.

The storage 107 stores the template information DB 107a. FIG. 9 is a diagram showing one example of content of the template information DB 107a. In the template information DB 107a, data such as template identification information, template image information, a characteristic amount, the degree of similarity, information representing being selected, and the like is stored. In the template identification information, identification information used for uniquely identifying the template 210 is stored. In the template image information, image data of the template 210 is stored. In the characteristic amount, data representing a characteristic of the template 210 is stored. In the characteristic amount, for example, data of a length L, a width T, an angle $\theta$, an angle $\varphi$, an angle $\eta$, a size M, and the like may be included. The angle $\theta$, the angle $\varphi$, and the angle $\eta$ are posture parameters representing the posture of the marker MK. The length L, the width T, and the size M are data representing characteristics of the marker MK other than the posture. In the degree of similarity, for example, data representing the degree of similarity between the template 210 and at least one template 210 other than the template 210 is stored. In the information representing being selected, data representing the template 210 is in a selected state is stored.

Templates 210 of ID_i, ID_j, ID_k, and ID_l represented in the field of the template identification information, for example, are examples of the templates acquired by changing the angle θ. FIG. 7 is one example of a case in which each of the templates 210 described above is displayed.

Next, one example of the flow of a treatment using the medical treatment system 1 according to this embodiment will be described. The flow of this treatment is largely divided into a treatment plan generating stage, a template selection stage, and a treatment stage.

[Treatment Plan Generating Stage]

A treatment plan is generated in advance (for example, before about one week) for a treatment day. In the generation of a treatment plan, CT photographing is executed, and three-dimensional information of the inside of the body of the subject P including the position, the shape, and the size of a tumor inside the subject P is acquired. Then, on the basis of the three-dimensional information, emission conditions (an emission position, an emission timing, and the like) of the treatment beam for the subject P are set.

[Template Selection Stage]

The selection of the selection template 230 is performed immediately before a treatment using the treatment beam B and after the determination of the position of the subject P with respect to the radiation emitting apparatus 10 (i.e., determination of the position of the bed 11 at which the subject P is laid) is performed. Here, the determination of the position of the subject P, for example, is performed in the following flow. First, in a state in which the subject P is laid on the bed 11, the fluoroscopic images of the subject P is acquired using the radiation sources 12-1 and 12-2 and the radiation detectors 13-1 and 13-2. Then, in order to match the positions of a tumor and bones disposed inside the subject P included in this fluoroscopic images with the positions of a tumor and bones inside the subject P in the treatment plan, the fluoroscopic images and a digitally reconstructed radiograph (DRR) that is a fluoroscopic image virtually recovered from the three-dimensional CT image photographed in the treatment plan generating stage are combined. In this way, a deviation between the position of the subject P at the current time point and the position of the subject P in the treatment plan is acquired. The positional deviation of the subject P is acquired by retrieving the position of the CT image in which a DDR that is the most similar to the fluoroscopic image is recovered. Then, the bed 11 is moved such that the positional deviation of the subject P disappears. After the bed 11 is moved, fluoroscopic images of the subject P are reacquired using the radiation sources 12-1 and 12-2 and the radiation detectors 13-1 and 13-2. Then, the reacquired fluoroscopic images are collated with the DDR, and, in a case in which the positional deviation of the subject P is within a threshold, the determination of the position of the subject P is completed.

In this embodiment, the process of selecting the selection template 230 from the plurality of candidate templates 220 is performed after the determination of the position of the subject P. In other words, the process of selecting the selection template 230 is performed after the determination of the position of the subject P based on the image IM acquired by the image acquirer 102. In this embodiment, the process of selecting the selection template 230 is performed after the positioning of the subject P at a position at which the marker image MKI disposed inside the subject P is included in the image IM acquired by the image acquirer 102. When seen from a different viewpoint, after the subject P is positioned at a position at which the marker image MKI included in the image IM acquired by the image acquirer 102 can be compared with the marker correspondence area (i.e., first area Z1) included in the template 210, the process of selecting the selection template 230 is performed.

Figure 10:
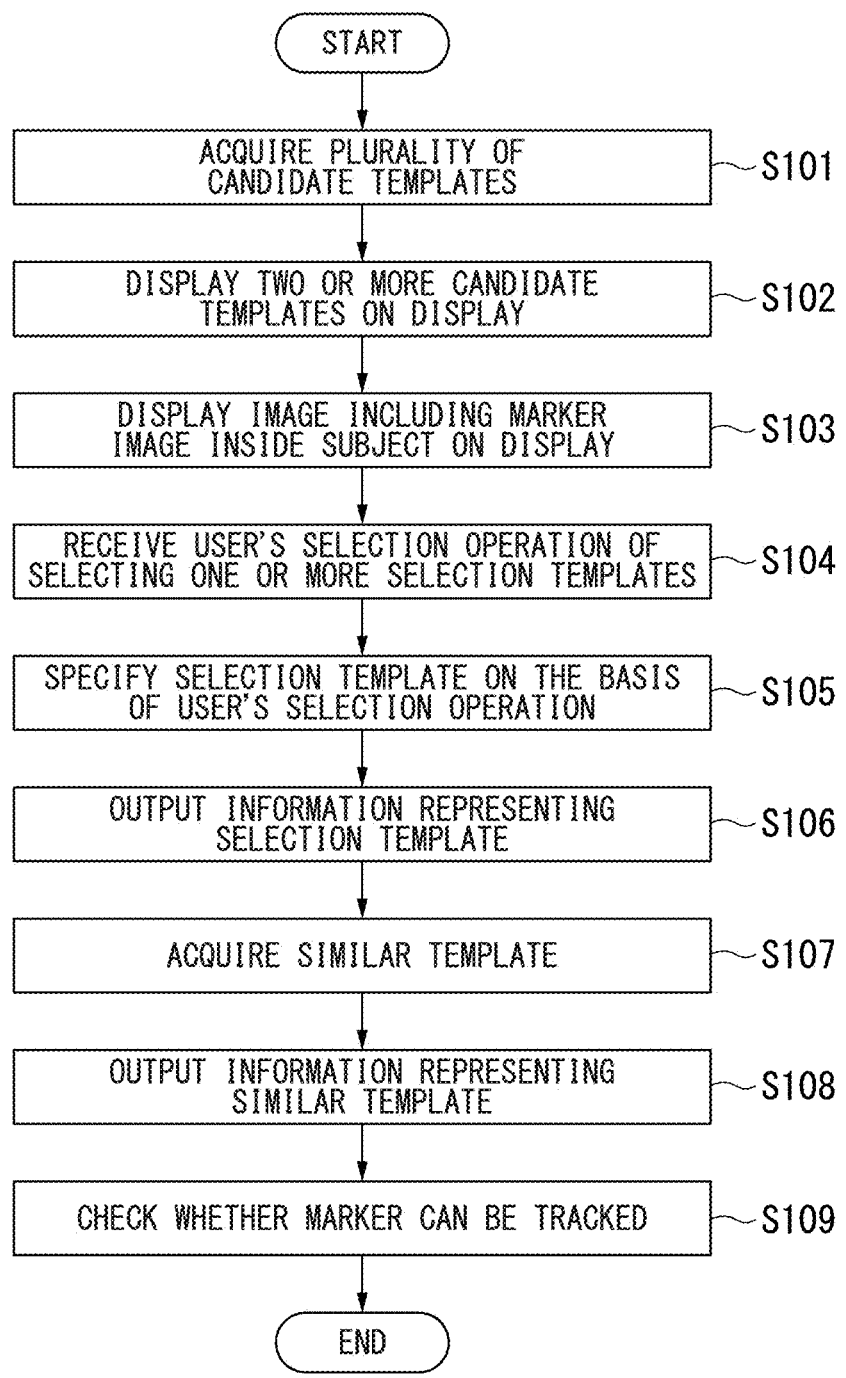
FIG. 10 is a flowchart showing one example of the flow of a process of selecting a selection template 230 according to the first embodiment.

FIG. 10 is a flowchart showing one example of the flow of the process of selecting the selection template 230. First, the template acquirer 101 acquires a plurality of candidate templates 220 (S101). This process of S101 may be performed before the determination of the position of the subject P or the generation of a treatment plan. The template acquirer 101 may directly output the plurality of acquired candidate templates 220 to the template selector 104 or the display processor 106 or may store the candidate templates in the template information DB 107a of the storage 107.

Next, the display processor 106 displays two or more candidate templates 220 among the plurality of candidate templates 220 acquired by the template acquirer 101 on the template selection image display area Z111 of the display 1032 (S102). In addition, the display processor 106 displays an image IM including the marker image MKI disposed inside the subject P acquired by the image acquirer 102 in the image display area Z112 of the display 1032 (S103). Accordingly, a user can review a selection template 230 to be selected from among two or more candidate templates 220 while viewing the image IM including the marker image MKI disposed inside the subject P. In addition, the image IM including the marker image MKI displayed on the display 1032 in S103 may be the image IM (for example, a fluoroscopic image that is reacquired for checking that the positional deviation of the subject P is within the threshold in a final stage of the determination of the position of the subject P) acquired for determining the position of the subject P, the image IM acquired by the image acquirer 102 again after the completion of the determination of the position of the subject P, or an image IM captured at the time of performing a treatment in the past. The process of S102 and the process of S103 may be simultaneously performed, or any one thereof may be performed first.

Next, the input receiver 1031 receives a user's selection operation of selecting one or more selection templates 230 in the state in which two or more candidate templates 220 and the image IM including the marker image MKI are displayed on the display 1032 (S104). Next, the template selector 104 specifies one or more selection templates 230 on the basis of the user's selection operation (S105). The template selector 104 outputs information representing the specified selection templates 230 to the tracker 105 and the template acquirer 101 (S106).

Next, the template acquirer 101 acquires one or more similar templates 250 on the basis of the content (for example, parameters (for example, the posture parameters (θ, φ, and η)) defining the selection template 230) of the selection template 230 specified by the template selector 104 (S107).

Figure 11:
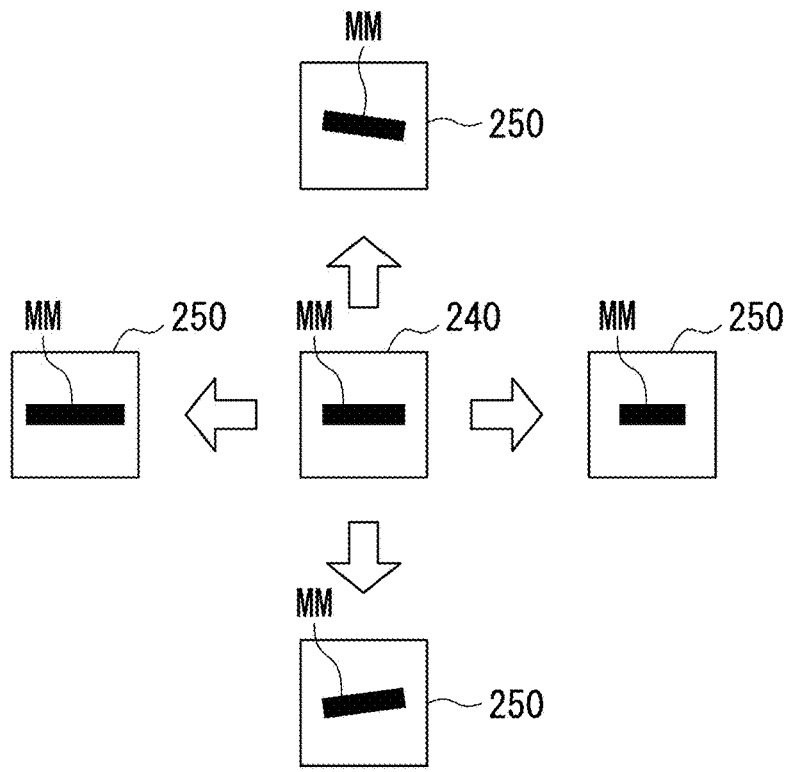
FIG. 11 is a diagram showing similar templates 250 according to the first embodiment.

FIG. 11 is a diagram showing similar templates 250. As shown in FIG. 11, for example, the template acquirer 101 acquires one or more similar templates 250 by using the selection template 230 specified by the template selector 104 as a reference template 240 and finely changing one or more parameters (for example, the posture parameters (θ, φ, and η)) defining the reference template 240. Here, the term "the finely changing of the parameters," for example, is a change in the parameter in a range in which the similar template 250 is more similar to the selected selection template 230 than candidate templates 220 that have not been selected from among two or more candidate templates displayed on the display 1032. The term "finely changing of the parameters," for example, is a change for absorbing an error in the size or the direction of the marker image IMK due to physiological phenomena of the subject P or an error in the determination of the position of the subject P. For example, the template acquirer 101 acquires one or more similar templates 250 acquired by finely changing the parameter θ, one or more similar templates 250 acquired by finely changing the parameter φ, and one or more similar templates 250 acquired by finely changing the parameter η by using the selection template 230 selected by the template selector 104 as the reference. In addition, the similar template 250 may be a template that is included in the plurality of candidate templates 220 that are initially acquired by the template acquirer 101. In other words, the similar template 250 may not be a template that is generated after the selection template 230 is selected. The template acquirer 101 outputs information representing the similar templates 250 to the tracker 105 (S108).

Thereafter, it is checked whether or not the marker MK can be tracked by the tracker 105 (S109). In other words, it is checked whether or not the tracker 105 can track the marker MK by using the image IM acquired by the image acquirer 102 at the predetermined interval (i.e., at the predetermined period), the selection templates 230, and the similar templates 250. This checking, for example, is performed over a time length corresponding to several times of respiration of the subject P. In a case in which it is checked that the marker MK can be tracked by the tracker 105, a series of processes relating to the selection of the template 210 is ended.

[Treatment Stage]

Figure 12:
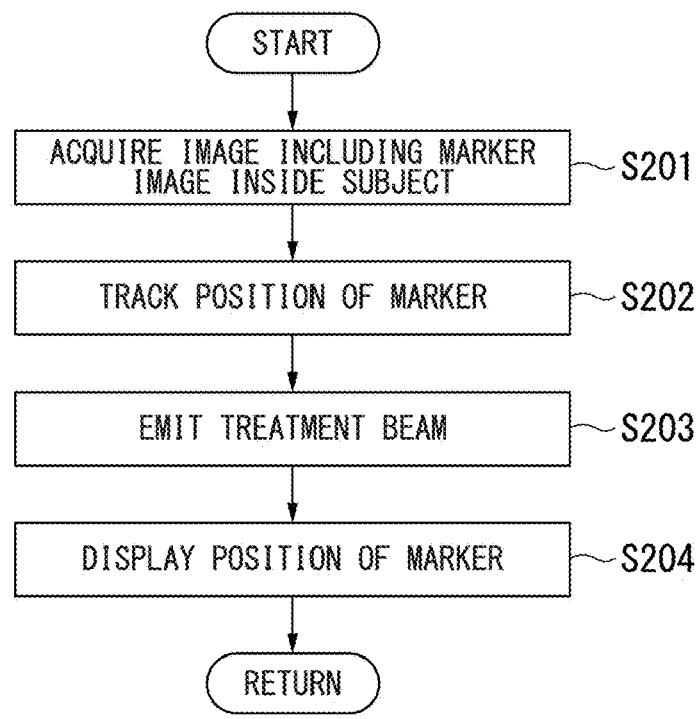
FIG. 12 is a flowchart showing one example of the flow of a process in a treatment stage according to the first embodiment.

FIG. 12 is a flowchart showing one example of the flow of the process in a treatment stage. As shown in FIG. 12, the image acquirer 102 acquires an image IM including the marker MK disposed inside the subject P at a predetermined interval (i.e., at the predetermined period) (S201). The image acquirer 102 outputs the acquired images IM to the tracker 105 and the display processor 106.

The tracker 105 tracks the position of the marker MK disposed inside the subject P by using the selection templates 230 specified by the template selector 104 and the similar templates 250 acquired by the template acquirer 101 (S202). In other words, the tracker 105 tracks the position of the marker MK disposed inside the subject P by scanning the image IM using the selection templates 230 and the similar templates 250. The tracker 105 outputs the tracked position of the marker MK disposed inside the subject P to the radiation emitting apparatus 10 and the display processor 106.

The controller 15 of the radiation emitting apparatus 10 executes control of the emission gate 14 to emit the treatment beam B on the basis of the position of the marker MK disposed inside the subject P that is tracked by the tracker 105. For example, in a case in which the marker MK disposed inside the subject P that is tracked by the tracker 105 enters a predetermined area, the controller 15 emits the treatment beam B by controlling the emission gate 14 (for example, by transmitting a control signal to the emission gate 14) (S203). The predetermined area is set on the basis of the relation between the position of a tumor and the position of the marker MK acquired in the treatment plan, the PTV, and the like. For example, a three-dimensional area acquired by adding a margin to the position of the marker MK on the CT image as the center corresponds to the predetermined area. In addition, an area acquired by projecting this area on the image IM may be set as the predetermined area. Furthermore, the predetermined area may be set in accordance with a margin added at that time in consideration of the state of the subject P immediately before the treatment.

The display processor 106 generates information associating the image IM acquired at the predetermined period by the image acquirer 102 with the position of the marker MK tracked by the tracker 105 and displays the generated information on the display 1032 (S204). Here, the process of S203 and the process of S204 may be simultaneously performed, or any one thereof may be performed first. The processes of S201 to S204 described above are repeatedly continued until the treatment ends.

According to the embodiment as described above, the information processing apparatus 100 includes the image acquirer 102, the template selector 104, and the tracker 105. The template selector 104 specifies at least one selection template 230 or more of which the number is smaller than the number of the plurality of candidate templates 220 among the plurality of candidate templates 220 relating to the marker MK on the basis of a user's input operation. The tracker 105 tracks the marker MK included in the image IM acquired by the image acquirer 102 by using at least one selection template 230 specified by the template selector 104.

According to such a configuration, on the basis of the user's input operation, the marker MK can be tracked using the selection templates 230 that have been narrowed down among the plurality of candidate templates 220. For this reason, the calculation load of the information processing apparatus 100 can be decreased to be less than that of a case in which the marker MK is scanned using all the candidate templates 220. In this way, the real timeliness of tracking of the marker MK can be further improved. For this reason, improvement in the tracking accuracy of the marker MK can be achieved as well. In addition, when seen from a different viewpoint, the marker MK is tracked using the selection templates 230 that are narrowed down from among the plurality of candidate templates 220, and accordingly, it can be avoided that a template having a high degree of similarity with a portion other than the marker is used for the tracking. For this reason, the possibility of detecting an error in the tracking can be lowered. Also from such a viewpoint, further improvement in the tracking accuracy of the marker MK can be achieved.

In this embodiment, the input receiver 1031 receives a user's selection operation (i.e., designation operation) of selecting (i.e., designating) at least one selection template 230 included in the plurality of candidate templates 220 as the user's input operation. The template selector 104 specifies at least one selection template 230 on the basis of the user's selection operation received by the input receiver 1031. According to such a configuration, a selection template 230 having a high degree of similarity with the marker image MKI can be directly designated by the user. Accordingly, scanning can be performed using the selection template 230 that is more similar to the marker image MKI, and further improvement in the tracking accuracy of the marker MK can be achieved.

In this embodiment, the information processing apparatus 100 further includes the display processor 106 that displays two or more candidate templates 220 included in the plurality of candidate templates 220 on the display 1032. The input receiver 1031 receives a user's selection operation of selecting one or more selection templates 230 from among two or more candidate templates 220 displayed on the display 1032. According to such a configuration, a user can select a selection template 230 by referring to the marker image MKI disposed inside the subject P displayed on the display 1032. In this way, a selection template 230 that is more similar to the marker image MKI can be selected by the user. Accordingly, further improvement in the tracking accuracy of the marker MK can be achieved.

In this embodiment, the input receiver 1031 receives the user's selection operation in the state in which the image IM including the marker image MKI disposed inside the subject P is displayed on the display 1032 by the display processor 106. According to such a configuration, a user can select a selection template 230 while observing the marker image MKI disposed inside the subject P displayed on the display 1032. Accordingly, a selection template 230 that is more similar to the marker image MKI can be selected by the user.

In this embodiment, the input receiver 1031 receives a user's input operation. The template selector 104 specifies at least one selection template 230 out of a plurality of templates 210 relating to the shape of the marker MK disposed inside the subject on the basis of the user's input operation received by the input receiver 1031. The tracker 105 tracks the marker MK inside an image including the marker MK by using at least one selection template 230 that has been specified. Accordingly, further improvement in the tracking accuracy of the marker MK can be achieved.

However, the embodiment is not limited to the example described above. For example, the method of tracking the marker MK using the tracker 105 is not limited to the example described above. For example, the tracker 105 may track the marker MK by using only the selection template 230 specified by the template selector 104 without using the similar templates 250 acquired by the template acquirer 101.

In addition, the template acquirer 101 outputs information representing a similar template 250 similar to at least one selection template 230 specified by the template selector 104. For example, the template acquirer 101 acquires one or more similar templates 250 of which one or more parameters defining at least one selection template 230 have been changed on the basis of the content of the at least one selection template 230 specified by the template selector 104. In this case, in a case in which the similar template 250 is more similar to the marker MK disposed inside the image IM than at least one selection template 230 specified by the template selector 104, the marker MK is tracked by using the similar template 250. At that time, the tracker 105 may track the marker MK by using the at least one selection template 230 specified by the template selector 104 and one or more similar templates 250 acquired by the template acquirer 101. According to such a configuration, even in a case in which the shape of the marker image MKI is changed in accordance with respiratory movement inside the body, variations in the heart beat, or the like, the marker MK can be tracked using the similar template 250 with high accuracy.

Next, several modified examples of the first embodiment will be described. In the configuration of each modified example, configurations other than configurations described below are similar to those of the first embodiment.

First Modified Example

Figure 13:
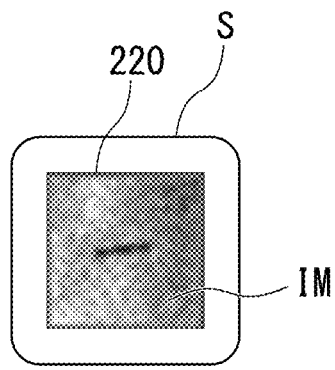
FIG. 13 is a diagram showing one example of a content of a template selection screen S according to a first modified example of the first embodiment.

FIG. 13 is a diagram showing one example of content of a template selection screen S according to a first modified example. As shown in FIG. 13, the display processor 106 according to this modified example displays two or more candidate templates 220 (in FIG. 13, only one candidate template 220 is shown) on the display 1032. For example, the display processor 106 displays one or two or more candidate templates 220 on the template selection screen S of the display 1032 in a state in which the candidate templates 220 are superimposed on images IM acquired by the image acquirer 102. For example, the display processor 106 displays, on the display 1032, a candidate template 220 (i.e., a first candidate template) among two or more candidate templates 220 in a state in which the first candidate template is superimposed on the image IM including the maker image MKI and another candidate template 220 (i.e., a second candidate template) among two or more candidate templates 220 in a state in which the second candidate template is superimposed on the image IM including the maker image MKI. In this case, the display processor 106 may compose an image acquired by cutting out the image IM at an arbitrary position before a treatment, which is acquired by the image acquirer 102, and a binarized image of the candidate template 220 through an image composing process such as a blending or the like and display the composed image on the template selection screen S. The a blending is one method used in an image composing process for overlapping two images, and, according to the a blending, another image can be overlapped with a specific position of an image that becomes a background. In addition, the display processor 106 may display two or more candidate templates 220 on the display 1032 in a state in which the candidate templates 220 are superimposed on the images IM.

According to such a configuration, the user can view the candidate templates 220 in a state in which the candidate templates 220 can be easily compared with the marker image MKI included in the image IM of the actual subject P acquired by the image acquirer 102. In this way, the selection template 230 that is more similar to the marker image MKI can be selected by the user. Accordingly, further improvement in the tracking accuracy of the marker MK can be achieved.

Second Modified Example

Figure 14:
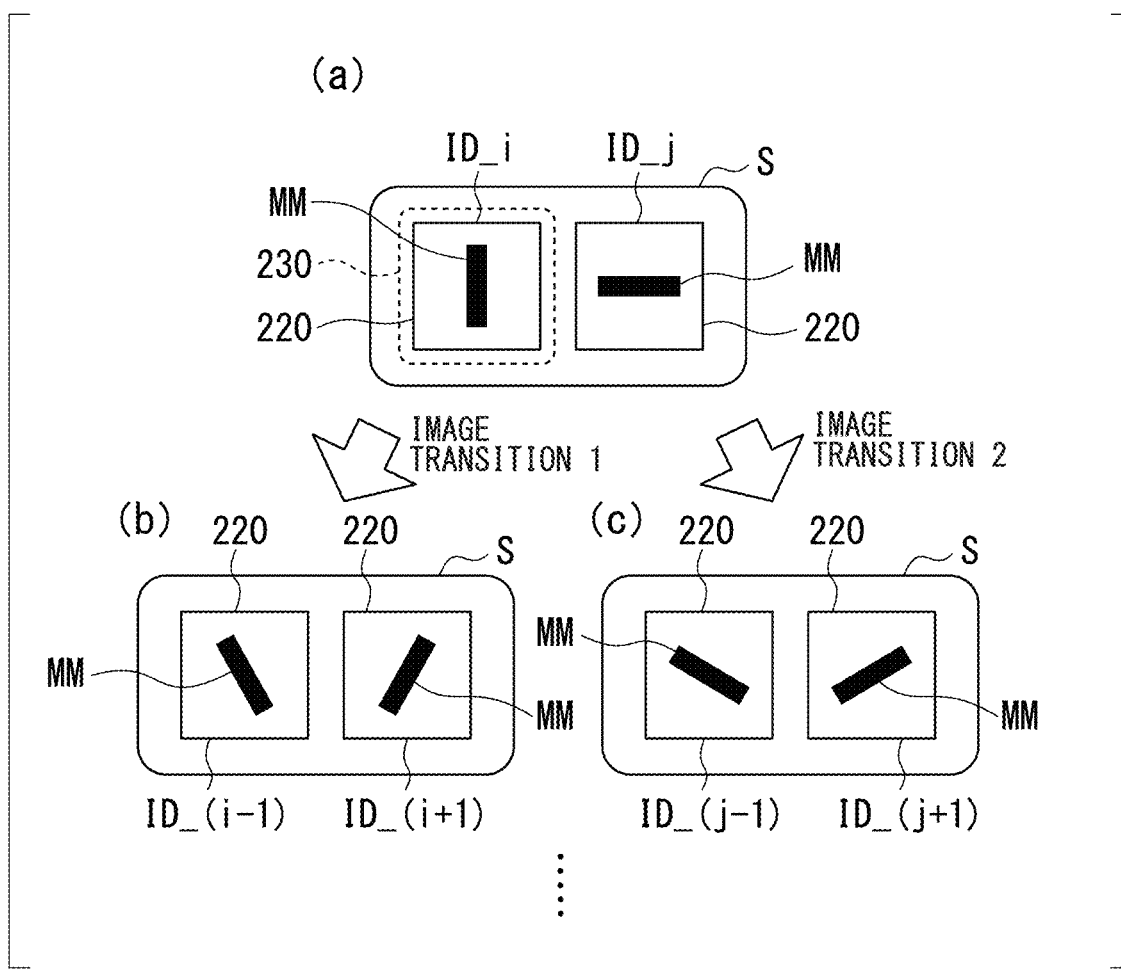
FIG. 14 is a diagram showing one example of a content of template selection screens S according to a second modified example of the first embodiment.

FIG. 14 is a diagram showing one example of content of template selection screens S according to a second modified example. As shown in (a) in FIG. 14A, in this modified example, the display processor 106 displays a first template (ID_i) and a second template (ID_j) included in at least a plurality of candidate templates 220 on the display 1032. For example, on the template selection screen S, two candidate templates 220 (the first template (ID_i) and the second template (ID_j)) of which the directions of the rectangles MM inside the templates 210 are different are aligned to be displayed. The two candidate templates 220 are templates included in the plurality of candidate templates 220 acquired by the template acquirer 101. Then, the input receiver 1031 receives a user's selection operation of selecting one of the two candidate templates 220 displayed on the template selection screen S.

In a case in which the user selects the first template (ID_i), and a selection operation thereof is detected by the input receiver 1031, the template selector 104 specifies the template (ID_i) without specifying the template (ID_j). In this case, the template selector 104 selects other candidate templates 220 (a third template (ID_(i−1)) and a fourth template (ID_(i+1))) that are more similar to the selected (i.e., specified) template (ID_i) than to the template (ID_j) that has not been selected (i.e., has not been specified) among the plurality of candidate templates 220 as candidate templates 220 to be displayed next on the template selection screen S. Accordingly, the display processor 106 can display other candidate templates 220 (the template (ID_(i−1)) and the template (ID_(i+1))) more similar to the template (ID_i) than to the template (ID_j) among the plurality of candidate templates 220 on the display 1032. Here, the template (ID_(i−1)) is one example of a "third template", and the template (ID_(i+1)) is one example of a "fourth template".

As shown in (b) in FIG. 14, next, the display processor 106 transitions the template selection screen S to the next screen (e.g., transition screen 1). On this transition screen 1, two candidate templates 220 (the template (ID_(i−1)) and the template (ID_(i+1))) that are more similar to the selected template (ID_i) than to the template (ID_j) that has not been selected in the previous selection operation are displayed. Then, the input receiver 1031 receives a user's selection operation of selecting one of two candidate templates 220 displayed on the transition screen 1. In addition, the input receiver 1031 may receive a user's selection operation representing selection of whether to select a new candidate template 220 or to select the candidate template 220 selected by the previous selection operation.

Although the description presented above shows an example in which the user selects the first template (ID_i), this similarly applies also in a case in which the user selects the second template (ID_j). In such a case, the display processor 106, as shown in (c) in FIG. 4, transitions the template selection screen S to another transition screen 2 that is different from the transition screen 1. In this transition screen 2, two candidate templates 220 (a template (ID_(j−1)) and a template (ID_(j+1))) that are more similar to the selected (i.e., specified) template (ID_j) than to the template (ID_i) that has not been selected (i.e., has not been specified) in the previous selection operation are displayed. Then, the input receiver 1031 receives a user's selection operation of selecting one of the two candidate templates 220 displayed on the transition screen 2. In addition, the input receiver 1031 may receive a user's selection operation representing selection of a new candidate template 220 or selection of the candidate template 220 selected in the previous selection operation.

The information processing apparatus 100 repeats the process of receiving the selection described above and specifies a selection template 230 to be used for tracking in a stage in which the selection of a new candidate template 220 is not required. While the description presented above relates to a two-selection system of a two-item opposition type, the number of candidate templates 220 displayed once may be increased to be three or more, and a system (e.g., one-selection system of multiple items type) for designating one selection template 230 from among more candidates may be employed.

According to such a configuration, since the number of candidate templates 220 displayed on the template selection screen S once is limited, the user can relatively easily determine a candidate template 220 that is similar to the marker image MKI. For this reason, the user can easily select a selection template 230 having a higher degree of similarity with the marker image MKI. Accordingly, further improvement in the tracking accuracy of the marker MK can be achieved. Here, the transition screen 1 may display the third template (for example, the template (ID_(i−1))) and the template (for example, the template (ID_i)) that is selected in the previous selection operation instead of displaying the third template and the fourth template.

Third Modified Example

Figure 15:
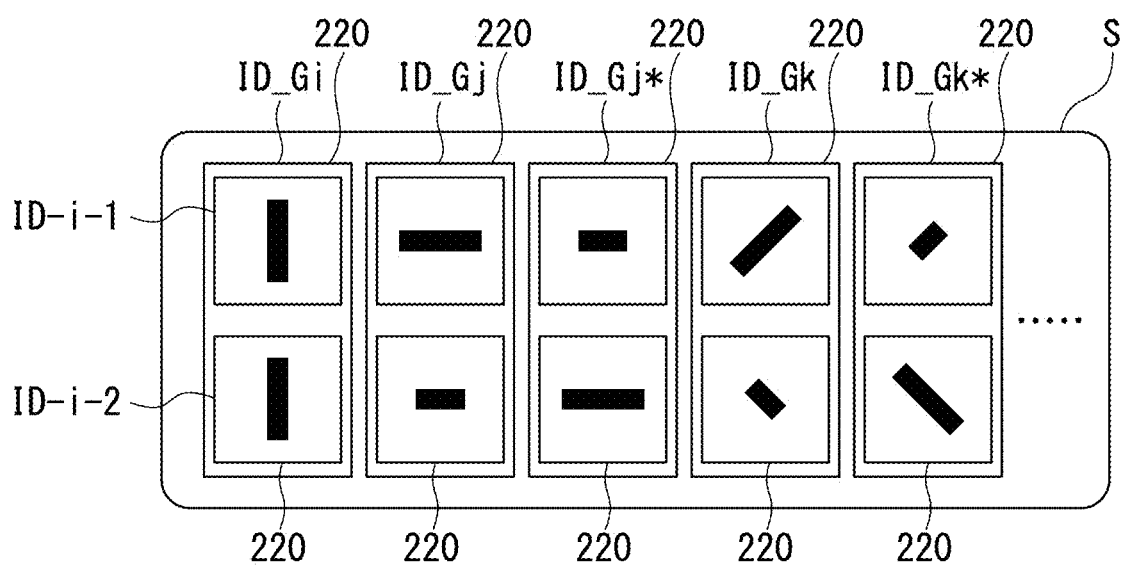
FIG. 15 is a diagram showing one example of a content of a template selection screen S according to a third modified example of the first embodiment.

FIG. 15 is a diagram showing one example of the content of a template selection screen S according to a third modified example. As shown in FIG. 15, in this modified example, a plurality of candidate templates 220 that are visually different from each other are displayed on the template selection screen S. The plurality of candidate templates 220 shown in FIG. 15 are candidate templates to be selected by a user. A difference from the example shown in FIG. 6 is that, in a case in which two sets of radiation sources and radiation detectors, in other words, a radiation source 12-1 and a radiation detector 13-1 and a radiation source 12-1 and a radiation detector 13-2 are present, a plurality of sets of candidate templates 220 corresponding to each set of marker images MKI generated by each detector are displayed.

For example, ID_Gi, ID_Gj, ID_Gj*, ID_Gk, ID_Gk*, and the like are identification information (i.e., template set identification information) of candidate templates 220 of one set (i.e., template set). In a template set identified by ID_Gi, two candidate templates 220 of ID_i−1 and ID_i−2 are included. This similarly applies to other sets.

The candidate templates 220 of one set, for example, are managed using the template information DB 107a shown in FIG. 16. FIG. 16 is a diagram showing a template information DB 107a according to this modified example. In the template information DB 107a shown in FIG. 16, data of template set identification information, template identification information, template image information, a characteristic amount, the degree of similarity, in middle of selection, and the like is stored. Information relating to a template set identified by a plurality of pieces of template identification information is associated with the template set identification information.

According to this modified example, by handling a plurality of images IM of which the capturing directions are different as a set, a candidate template 220 similar to the posture of the marker MK in the three-dimensional space can be easily retrieved.

Fourth Modified Example

Figure 17:
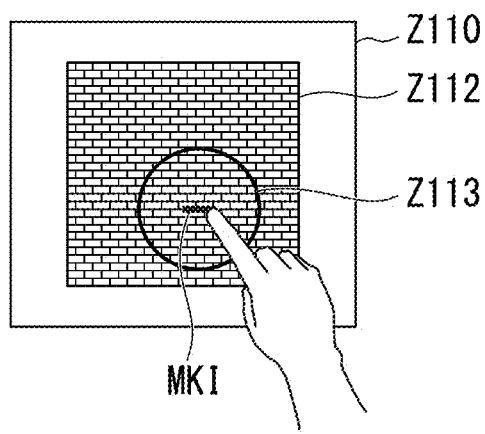
FIG. 17 is a diagram showing one example of a content of an operation screen Z110 according to a fourth modified example of the first embodiment.
Figure 18:
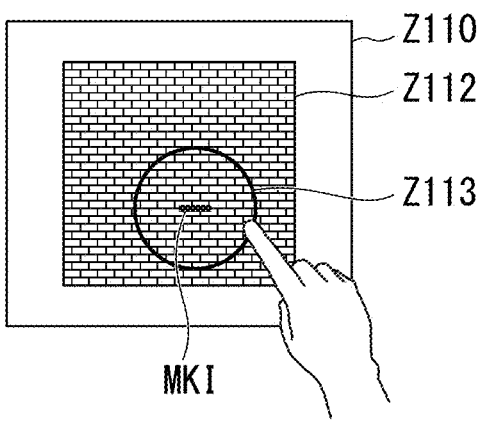
FIG. 18 is a diagram showing one example of the content of the operation screen Z110 according to the fourth modified example of the first embodiment.

FIGS. 17 and 18 are diagrams showing one example of the content of an operation screen Z110 according to a fourth modified example. As shown in FIGS. 17 and 18, in this modified example, an image display area Z112 is assigned to an operation screen Z110 of the input/display unit 103, and a template selection image display area Z111 is not assigned. As the display of the operation screen Z110, only the image IM may be displayed. In other words, the display processor 106 displays only the image IM on the operation screen Z110 of the input/display unit 103 and may not display a candidate template 220.

For example, a user touches the vicinity of the marker image MKI on the image IM displayed on the operation screen Z110 of the input/display unit 103 instead of selecting a selection template 230, thereby designating the position of the marker image MKI in the image IM. For example, as shown in FIG. 17, the user designates one point overlapping with the marker image MKI in the image IM or on the vicinity thereof.

In a case in which one point is designated as such, the template selector 104 extracts a partial area Z113, which has a predetermined size, including the one point. The predetermined size, for example, may be determined in advance on the basis of the size of the marker MK placed inside the subject P. The template selector 104 selects a candidate template 220 that is the most similar to the marker image MKI from among a plurality of candidate templates 220 as a selection template 230 for the image IM disposed inside the partial area Z113 including the marker image MKI. As the degree of similarity of the candidate template 220 for the image IM, a normalized cross correlation, a mutual information amount, or the degree of separation described above is used.

Instead of designating one point, a range of the partial area Z113 in the image IM may be designated. In such a case, for example, as shown in FIG. 18, the user traces the edge of an area including the marker image MKI therein, thereby designating the partial area Z113 in the image IM as a range. The template selector 104 associates the range with the partial area Z113 having the predetermined size. Then, the template selector 104 selects a candidate template 220 that is the most similar to the marker image MKI from among a plurality of candidate templates 220 as a selection template 230 for the image IM disposed inside the partial area Z113.

More specifically, the template selector 104 may perform the following process. For example, the template selector 104 selects at least one selection template 230 on the basis of the degrees of similarity of one or more candidate templates 220 included in a plurality of templates 210 for the partial area Z113 including one point inside the image IM or the partial area Z113 of the image IM in the case of the designation of a range.

For example, the template selector 104 may select at least one selection template 230 on the basis of the threshold of the degree of similarity. In other words, the template selector 104 may select a candidate template 220 of which the degree of similarity is the threshold or more as a selection template 230. In this way, the template selector 104 can select a selection template 230 of which the degree of similarity with the marker image MKI is high.

In addition, instead of the description presented above, the template selector 104 derives the degree of similarity of each of two or more candidate templates 220 for the partial area Z113 including one point disposed inside the image IM or the partial area Z113 of the image IM in the case of designation of a range. Furthermore, the template selector 104 may select at least one selection template 230 out of two or more candidate templates 220 in order of highest to lowest degree of similarity. Accordingly, the template selector 104 can select a selection template 230 having a high degree of similarity with the marker image MKI.

In other words, in this modified example, the display processor 106 displays the image IM acquired by the image acquirer 102 on the display 1032. The input receiver 1031 receives a designation operation of designating one point in the image IM or a partial area of the image IM which are displayed on the display 1032 as a user's input operation. The template selector 104 selects at least one selection template 230 on the basis of the user's designation operation received by the input receiver 1031. Accordingly, the user can cause the information processing apparatus 100 to select a selection template 230 without performing a selection operation of selecting the selection template 230 among a plurality of candidate templates 220. Accordingly, the user's convenience is improved.

Second Embodiment

Next, a second embodiment will be described. An information processing apparatus 100 according to this embodiment uses not only a selected selection template 230 but performs dynamic switching between templates 210 at the time of tracking, which is different from the first embodiment. Owning to this configuration, even in a case in which the posture of a marker MK placed inside a subject P is greatly changed in accordance with respiratory movement inside the body, variations in the heart beat, or the like, a marker MK can be tracked with high accuracy. Configurations other than those described below are similar to those of the first embodiment described above.

Figure 19:
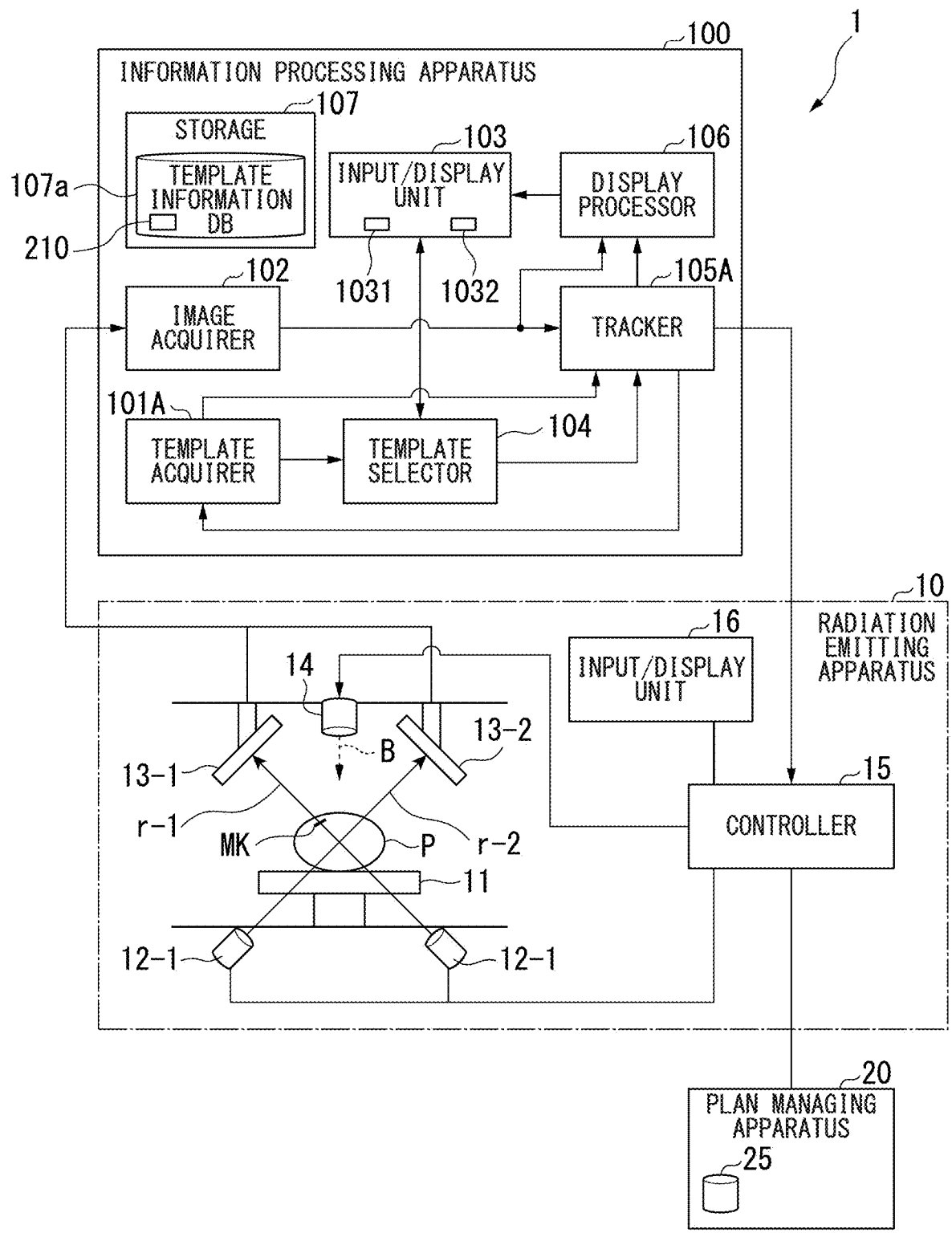
FIG. 19 is a diagram showing an example of the configuration of a medical treatment system 1 according to a second embodiment.

The functional configuration of the information processing apparatus 100 according to this embodiment will be described with reference to FIG. 19. FIG. 19 is a diagram showing an example of the configuration of a medical treatment system 1 according to the embodiment. The information processing apparatus 100 includes a template acquirer 101A, an image acquirer 102, an input/display unit 103, a template selector 104, a tracker 105A, and a display processor 106. Differences from the information processing apparatus 100 shown in FIG. 1 described above are the template acquirer 101A and the tracker 105A, and here, these will be focused in description.

The tracker 105A, first, similar to the tracker 105 according to the first embodiment, tracks a marker MK by using a selection template 230 selected or specified by the template selector 104 and one or more similar templates 250. Then, in this embodiment, the tracker 105A evaluates the degree of similarity of each of the selection template 230 and the one or more similar templates 250 with the marker image MKI during the tracking operation. Then, the tracker 105A specifies the selection template 230 or the similar template 250 of which the degree of similarity with the marker image MKI satisfies a predetermined condition (or example, the degree of similarity is maximum) as a specific template among the selection template 230 and the one or more similar templates 250. Here, the selection template 230 and the one or more similar templates 250 are one example of two or more templates included in a plurality of templates. Then, the tracker 105A outputs parameters (for example, posture parameters ($\theta$, $\varphi$, and $\eta$)) defining a specific template to the template acquirer 101A. In addition, instead of this, the tracker 105A may output information (for example, identification information of a specific template) representing the specific template to the template acquirer 101A or may output information representing the degree of similarity of each of the selection template 230 and the one or more similar templates 250 to the template acquirer 101A.

The template acquirer 101A sets the template (i.e., the specific template described above) of which the degree of similarity with the marker image MKI satisfies the predetermined condition (for example, the degree of similarity is maximum) among templates 210 used for tracking the marker MK by the tracker 105A as a new reference template 240 again. Then, the template acquirer 101A acquires one or more new similar templates 250 by finely changing one or more parameters (for example, the posture parameters ($\theta$, $\varphi$, and $\eta$)) defining the new reference template 240. The template acquirer 101A outputs information representing the new reference template 240 and the one or more new similar templates 250 that have been acquired to the tracker 105A.

Then, the tracker 105A performs switching between one or more templates 210 used for tracking the marker MK on the basis of the information output by the template acquirer 101A. For example, the tracker 105A tracks the marker MK on the basis of the new reference template 240 specified by the template acquirer 101A and the one or more new similar templates 250 that have been acquired. Thereafter, by repeating the process described above, the tracker 105A tracks the marker MK by sequentially changing (i.e., updating) the templates 210. In addition, the similar templates 250 may be templates included in a plurality of candidate templates 220 acquired initially by the template acquirer 101. In other words, the similar templates 250 may not be templates generated after the reference template 240 is newly set.

Figure 20:
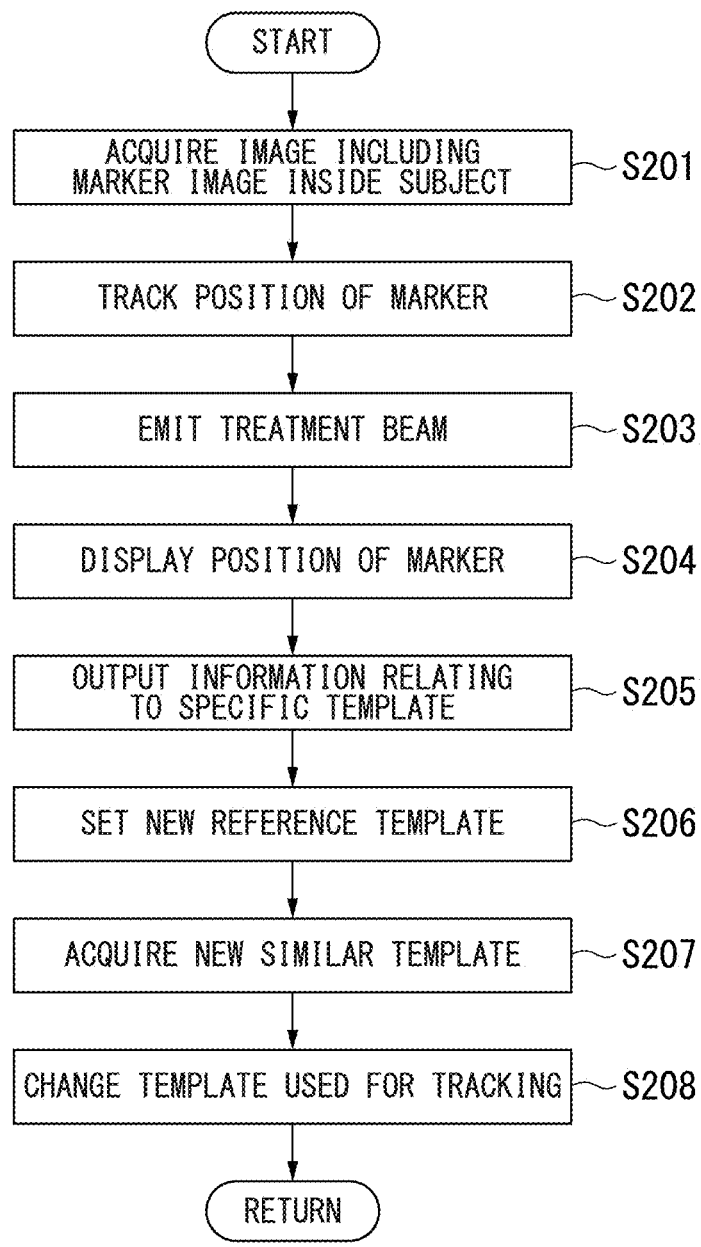
FIG. 20 is a flowchart showing one example of the flow of a process performed in a treatment stage according to the second embodiment.

FIG. 20 is a flowchart showing the flow of a process performed in a treatment stage according to this embodiment. The processes of S201 to S204 shown in FIG. 20 are similar to the processes of S201 to S204 according to the first embodiment.

In this embodiment, the tracker 105A, for example, outputs the information relating to parameters defining a specific template of which the degree of similarity with the marker image MKI satisfies a predetermined condition among the templates 210 used for tracking by the tracker 105A or information representing the specific template and the like as a result of tracking performed in advance (S205). For example, in the information output from the tracker 105A, parameters (for example, the posture parameters (θ, φ, and η)) defining the specific template are included.

Then, the template acquirer 101A sets the specific template described above to the new reference template 240 again (S206). Then, the template acquirer 101A acquires the one or more new similar templates 250 on the basis of the content of the new reference template 240 (S207). The tracker 105A performs switching between the templates 210 used for tracking the marker MK on the basis of the new reference template 240 specified by the template acquirer 101A and the one or more new similar templates 250 that have been acquired (S208).

According to this embodiment, not only the template 210 that is initially selected or specified is used, but switching among the templates 210 can be dynamically performed during the time of tracking. From this, even in a case in which the posture of the marker MK placed inside the subject P is greatly changed in accordance with respiratory movement inside the body, variations in the heart beat, or the like, the position of the marker MK can be tracked.

Third Embodiment

Next, a third embodiment will be described. An information processing apparatus 100 according to this embodiment displays the position of a marker MK tracked on an image IM and the position of a tumor estimated from the position of the marker MK such that the position of the marker MK and the position of the tumor can be checked by a user.

The functional configuration of the information processing apparatus 100 according to the embodiment will be described with reference to FIG. 1 described above. The information processing apparatus 100 includes a template acquirer 101, an image acquirer 102, an input/display unit 103, a template selector 104, a tracker 105, a display processor 106A, and a storage 107. A difference from the first embodiment described above is the display processor 106A, and here, the display processor 106A will be focused on in the description.

The display processor 106A acquires images IM from the image acquirer 102 and acquires the position of the marker MK from the tracker 105. The display processor 106A displays an indication H1 representing the position of the marker MK on the image IM.

Figure 21:
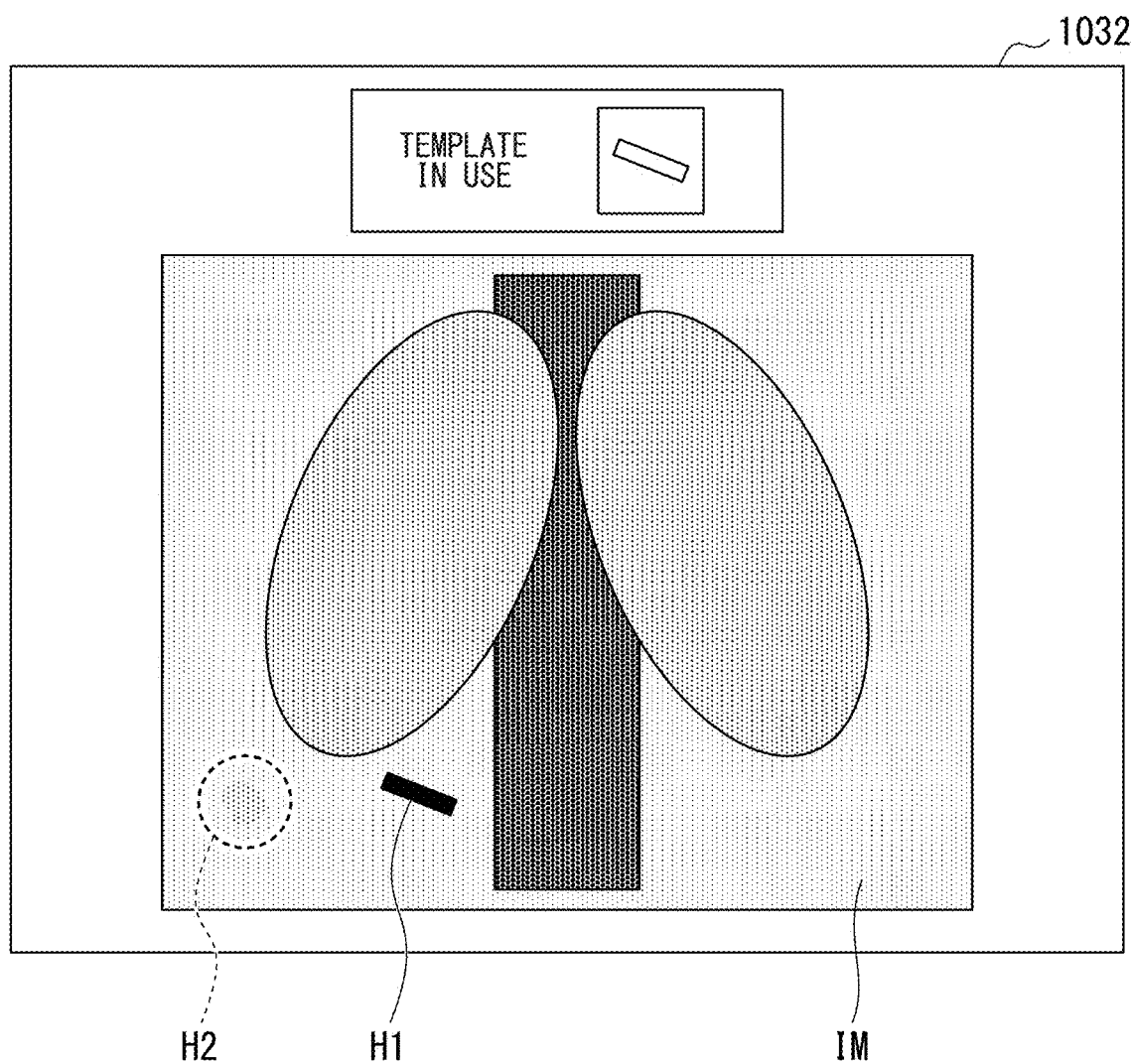
FIG. 21 is a diagram showing one example of an image IM displayed by a display processor 106A according to a third embodiment.

FIG. 21 is a diagram showing one example of an image IM displayed by the display processor 106A. As shown in FIG. 21, for example, the display processor 106A displays a rectangle MM of a template 201 representing the position of the marker MK on the image IM as the indication H1. At this time, the display processor 106A may display information representing the template 210 used for tracking the marker MK.

In this embodiment, the display processor 106A displays the position of a tumor estimated from the position of the marker MK in the image IM displayed on the display 1032. A method of estimating the position of the tumor from the position of the marker MK will be described. A tumor position y is calculated from the position $x_m$ of the marker MK by using Equation (1) representing a linear relation.

$$y = Ax_m + T \qquad (1)$$

In Equation (1) represented above, $x_m$ and y are vectors representing positions. A is a 2×2 matrix. T is 1×2 vector. A and T are determined using linear regression from the positions of one or more markers MK and the position of the tumor acquired before the treatment.

As the position of the marker MK and the position of the tumor, for example, the position of the tumor and the position of a marker MK appearing on a CT image photographed at the time of generating a treatment plan can be used. In other words, a relation between the position of the tumor and the position of the marker MK can be acquired by acquiring A and T represented in Equation (1) represented above using linear regression on the basis of a plurality of CT images (i.e., three-dimensional images) photographed during one respiration. For example, the relation between the position of the tumor and the position of the marker is acquired using linear regression from the center of gravity of the tumor area and the center of gravity of an area corresponding to the marker MK projected when a DRR is generated from the CT image.

The display processor 106A calculates the position of the tumor on the basis of the position of the marker MK tracked by the tracker 105 and Equation (1) represented above. Then, the display processor 106A displays the calculated position of the tumor on the image IM as an indication H2.

According to this embodiment, the position of the tumor that is estimated from the position of the marker MK is displayed on the image IM. Accordingly, a user can continue a treatment while easily checking the position of the tumor.

As above, while several embodiments and modified examples have been described, the embodiment is not limited to the examples described above. For example, in the embodiments and the modified examples described above, an example in which the marker MK having a bar shape placed inside the subject P is tracked has been described. However, the marker MK that is a tracking target may have a wedge shape or any other shape. For example, in a case in which a marker MK having a wedge shape is tracked, the shape of the template 210 is formed in a wedge shape. In addition, an "object" is not limited to a tumor or a marker MK and may be a catheter in a catheter operation. In such a case, by using a template 210 corresponding to the shape of the catheter, a catheter image appearing on the image IM of the subject P photographed during the operation can be tracked.

In addition, the tracker 105 may fix the number of templates 210 used during a treatment to one or may perform switching among a plurality of templates 210 in accordance with the state of the subject P. For example, the posture of the marker MK, which is included inside the subject P, in the three-dimensional space changes in accordance with the respiration of the subject P. The tracker 105 may approximate the motions of the subject P or the changes in the posture of the marker MK according to respiration as a respiration model that is modeled in association with to one period of respiration, select a template 210 corresponding to a phase based on of the period of the respiration model, and perform a tracking process of the marker MK.

In addition, as described above, instead of a case in which a plurality of candidate templates 220 are displayed on the display 1032, and a user's selection operation is received, the information processing apparatus 100 may receive a user's designation operation of designating one point or a part of the image IM acquired by the image acquirer 102 and select a selection template 230 on the basis of the designation operation. In addition, instead of this, the template selector 104 may acquire information relating to a treatment plan of the subject P, set a predetermined area in the image IM acquired by the image acquirer 102 on the basis of an approximate position of the marker MK included in the treatment plan, acquire the degree of similarity of each of all the candidate templates 220 for the predetermined area, and select a candidate template 220 of which the degree of similarity satisfies a predetermined condition (for example, the degree of similarity is maximum) as a selection template 230. In such a case, the user's designation operation is not necessary.

According to at least one embodiment described above, the information processing apparatus 100 includes an input receiver, a template selector, and a tracker. The input receiver 1031 receives a user's input operation. The template selector 104 specifies at least one selection template 230 out of a plurality of templates 210 relating to the shape of the marker MK disposed inside the subject on the basis of a user's input operation received by the input receiver 1031. The tracker 105 tracks the marker MK in an image including the marker MK by using the at least one selection template 230 that has been specified. According to such a configuration, improvement in the tracking accuracy of the object inside the subject can be achieved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The following is an information processing apparatus according to an aspect of the second embodiment.

An information processing apparatus including:

a template selector configured to perform at least one of: selecting, out of a plurality templates, at least one or more templates of which the number is smaller than the number of the plurality of templates based on an image of a subject acquired by an image acquirer; and specifying, out of a plurality templates, at least one or more templates of which the number is smaller than the number of the plurality of template based on a user's input operation;

a tracker configured to track an object in the image of the subject by using the at least one or more templates that are selected or specified by the template selector; and a template acquirer configured to output information of one or more templates selected from among the plurality of templates, wherein the tracker specifies a template of which the degree of similarity with the object inside the image satisfies a predetermined condition out of two or more templates included in the plurality of templates, the template acquirer outputs information representing a similar template similar to the template specified by the tracker, and the tracker changes one or more templates used for tracking the object on the basis of the information output by the template acquirer.

What is claimed is:

1. An information processing apparatus comprising:
a processor configured to:
control to display, on a display, two or more templates included in a plurality of templates that are related to a shape of a marker inside a subject;
control to receive an input operation of a user which is a user's selection operation of selecting one or more templates out of the two or more templates displayed on the display;
control to specify at least one template out of the plurality of templates based on the input operation; and
control to track the marker in an image including the marker by using the at least one template.

2. The information processing apparatus according to claim 1, wherein
the processor is configured to control to display the image on the display.

3. The information processing apparatus according to claim 2, wherein
the processor is configured to control to display the two or more templates superimposed on the image on the display.

4. The information processing apparatus according to claim 2, wherein the processor is configured to:
control to receive a designation operation for designating one point in the image or a partial area of the image displayed on the display as the input operation of the user, and
control to select the at least one template based on the designation operation of the user.

5. The information processing apparatus according to claim 4, wherein
the processor is configured to control to select the at least one template based on a degree of similarity with an area of the image including the one point in the image or the partial area of the image.

6. The information processing apparatus according to claim 5, wherein
the processor is configured to control to select the at least one template based on a threshold of the degree of similarity.

7. The information processing apparatus according to claim 1, wherein the processor is configured to:
control to display at least a first template and a second template out of the plurality of templates on the display, and
control to display a third template and a fourth template that have a greater similarity to the first template than to the second template on the display out of the plurality of templates in a case in which the first template is specified based on the user's selection operation without specifying the second template.

8. The information processing apparatus according to claim 1, wherein the processor is configured to:

control to output information representing a similar template having a similarity to the at least one template, and
control to track the marker by using the at least one template and the similar template.

9. The information processing apparatus according to claim 1, wherein
the processor is configured to control to display a position of the marker, the position of the marker being superimposed on an acquired image of a subject on the display.

10. The information processing apparatus according to claim 1, wherein the processor is configured to:
control to output information representing a similar template having a similarity to the at least one template, and
control to track the marker by using the similar template in a case in which the similar template has greater similarity to the marker in the image than the at least one template.

11. The information processing apparatus according to claim 1, wherein
the marker is a metal marker.

12. The information processing apparatus according to claim 1, wherein
the processor is configured to generate the plurality of templates based on a three-dimensional shape of the marker.

13. The information processing apparatus according to claim 1, wherein the subject is a patient.

14. The information processing apparatus according to claim 13, wherein the marker is a marker implanted to a body of the patient.

15. The information processing apparatus according to claim 13, wherein the marker is not part of a body of the patient.

16. The information processing apparatus according to claim 1, wherein the marker is an artificial marker.

17. The information processing apparatus according to claim 1, wherein the plurality of templates are generated based on a plurality of postures of images of the marker from directions different from one another.

18. An information processing system comprising:
a processor configured to:
control to display, on a display, two or more templates included in a plurality of templates that are related to a shape of a marker inside a subject;
control to receive an input operation of a user which is a user's selection operation of selecting one or more templates out of the two or more templates displayed on the display;
control to specify at least one template out of the plurality of templates based on the input operation;
control to track the marker in an image including the marker by using the at least one template; and
control to cause an emitter that emits energy based on a position of the marker.

19. A computer program product comprising a software program embodied on a non-transitory computer-readable storage medium, the software program being executable by a computer of an information processing system to cause the information processing system to perform:
displaying, on a display, two or more templates included in a plurality of templates that are related to a shape of a marker inside a subject;
receiving an input operation of a user which is a user's selection operation of selecting one or more templates out of the two or more templates displayed on the display;
specifying at least one template out of the plurality of templates based on the input operation; and
tracking the marker in an image including the marker by using the at least one template.

* * * * *